(12) United States Patent
Hashimshony et al.

(10) Patent No.: US 8,032,211 B2
(45) Date of Patent: Oct. 4, 2011

(54) PROBES, SYSTEMS, AND METHODS FOR EXAMINING TISSUE ACCORDING TO THE DIELECTRIC PROPERTIES THEREOF

(75) Inventors: Dan Hashimshony, Givat Ada (IL); Gil Cohen, Jerusalem (IL); Iddo Geltner, Herzlia (IL)

(73) Assignee: Dune Medical Devices Ltd., Caesaria (IL)

( * ) Notice: Subject to any disclaimer, the term of this patent is extended or adjusted under 35 U.S.C. 154(b) by 512 days.

(21) Appl. No.: 11/797,167

(22) Filed: May 1, 2007

(65) Prior Publication Data
US 2008/0021343 A1   Jan. 24, 2008

Related U.S. Application Data

(63) Continuation-in-part of application No. 11/705,143, filed on Feb. 12, 2007, which is a continuation-in-part of application No. 10/965,752, filed on Oct. 18, 2004, now Pat. No. 7,184,824, and a continuation-in-part of application No. 10/035,428, filed on Jan. 4, 2002, now Pat. No. 6,813,515, application No. 11/797,167, and a continuation-in-part of application No. PCT/IL2006/000392, filed on Mar. 29, 2006, application No. 11/797,167, and a continuation-in-part of application No. 10/567,581, filed as application No. PCT/IL2006/000015 on Jan. 4, 2006, application No. 11/797,167, and a continuation-in-part of application No. 10/558,831, filed as application No. PCT/IL2005/000330 on Mar. 23, 2005, now Pat. No. 7,720,532, application No. 11/797,167, and a continuation-in-part of application No. PCT/IL2006/000908, filed on Aug. 6, 2006, which is a continuation-in-part of application No. 11/350,102, filed on Feb. 9, 2006, and a continuation-in-part of application No. 11/196,732, filed on Aug. 4, 2005, application No. 11/797,167, and a continuation-in-part (Continued)

(51) Int. Cl.
*A61B 5/05* (2006.01)
(52) U.S. Cl. .................................................. 600/547
(58) Field of Classification Search .............. 600/547, 600/306, 554; 606/32–34, 41; 324/642–646, 324/632
See application file for complete search history.

(56) References Cited

U.S. PATENT DOCUMENTS 3,830,224 A   8/1974   Vanzetti et al.
(Continued)

FOREIGN PATENT DOCUMENTS

DE   3637549   5/1988
(Continued)

OTHER PUBLICATIONS

Official Action Dated Aug. 31, 2010 From the US Patent and Trademark Office Re. U.S. Appl. No. 11/350,102.

(Continued)

*Primary Examiner* — Max Hindenburg
*Assistant Examiner* — Brian Szmal

(57) ABSTRACT

The present invention relates to probes, systems, and methods for tissue characterization by its dielectric properties, wherein a physical feature of the probe is designed to define and delimit a tissue volume, at a tissue edge, where characterization takes place. Thus, the probe for tissue-edge characterization comprises: a first inner conductor, which comprises: proximal and distal ends, with respect to a tissue edge, along an x-axis; a first sharp edge, inherently associated with the proximal end; at least one feature, issuing from the first inner conductor, substantially at the proximal end, for forming at least one additional sharp edge, operative to enhance localized electrical fringe fields in the tissue, within a generally predefined tissue volume, at the tissue edge, the tissue volume being generally defined by physical parameters associated with the at least one feature; and a dielectric material, which encloses the conductor, in the y-z planes.

34 Claims, 25 Drawing Sheets

Related U.S. Application Data of application No. 11/487,431, filed on Jul. 17, 2006, now Pat. No. 7,809,425, which is acontinuation-in-part of application No. 10/891,750, filed on Jul. 15, 2004, now Pat. No. 7,082,325, application No. 11/797,167, and a continuation-in-part of application No. 10/298,196, filed on Nov. 18, 2002, now Pat. No. 7,505,811, and a continuation-in-part of application No. PCT/IL2007/000071, filed on Jan. 18, 2007.

(60) Provisional application No. 60/665,842, filed on Mar. 29, 2005, provisional application No. 60/641,081, filed on Jan. 4, 2005, provisional application No. 60/555,901, filed on Mar. 23, 2004, provisional application No. 60/759,555, filed on Jan. 18, 2006.

(56) References Cited

U.S. PATENT DOCUMENTS

| | | | |
|---|---|---|---|
| RE30,317 | E | 7/1980 | Luebbers et al. |
| 4,291,708 | A | 9/1981 | Frei et al. |
| 4,344,440 | A | 8/1982 | Aaby et al. |
| 4,458,694 | A | 7/1984 | Sollish et al. |
| 4,537,203 | A | 8/1985 | Machida |
| 4,539,640 | A | 9/1985 | Fry et al. |
| RE32,000 | E | 10/1985 | Sagi |
| 4,617,939 | A | 10/1986 | Brown et al. |
| 4,625,171 | A | 11/1986 | Sekihara et al. |
| 4,682,594 | A | 7/1987 | Mok |
| 4,689,567 | A | 8/1987 | Maudsley |
| 4,751,464 | A | 6/1988 | Bridges |
| 4,768,513 | A | 9/1988 | Suzuki |
| 4,779,624 | A | 10/1988 | Yokoi |
| 4,785,806 | A | 11/1988 | Deckelbaum |
| 5,115,137 | A | 5/1992 | Andersson-Engels et al. |
| 5,143,079 | A | 9/1992 | Frei et al. |
| 5,227,730 | A | 7/1993 | King et al. |
| 5,277,730 | A | 1/1994 | Darsey et al. |
| 5,334,941 | A | 8/1994 | King |
| 5,383,454 | A | 1/1995 | Bucholz |
| 5,442,290 | A | 8/1995 | Crooks |
| 5,482,041 | A | 1/1996 | Wilk et al. |
| 5,482,047 | A | 1/1996 | Nordgren et al. |
| 5,558,092 | A | 9/1996 | Unger et al. |
| 5,572,132 | A | 11/1996 | Pulyer et al. |
| 5,630,426 | A | 5/1997 | Eggers et al. |
| 5,678,565 | A | 10/1997 | Sarvazyan |
| 5,699,804 | A | 12/1997 | Rattner |
| 5,704,355 | A | 1/1998 | Bridges |
| 5,727,569 | A | 3/1998 | Benetti et al. |
| 5,735,278 | A | 4/1998 | Hoult et al. |
| 5,744,971 | A | 4/1998 | Chan et al. |
| 5,758,646 | A | 6/1998 | Van Der Meulen et al. |
| 5,800,350 | A | 9/1998 | Coppleson et al. |
| 5,807,257 | A | 9/1998 | Bridges |
| 5,810,742 | A | 9/1998 | Pearlman |
| 5,821,410 | A | 10/1998 | Xiang et al. |
| 5,829,437 | A | 11/1998 | Bridges et al. |
| 5,884,239 | A | 3/1999 | Romanik, Jr. |
| 5,900,618 | A | 5/1999 | Anlage et al. |
| 5,927,284 | A | 7/1999 | Borst et al. |
| 6,004,263 | A | 12/1999 | Nakaichi et al. |
| 6,010,455 | A | 1/2000 | Barnett et al. |
| 6,026,323 | A | 2/2000 | Skladnev et al. |
| 6,055,451 | A | 4/2000 | Bambot et al. |
| 6,055,452 | A | 4/2000 | Pearlman |
| 6,061,589 | A | 5/2000 | Bridges et al. |
| 6,071,239 | A | 6/2000 | Cribbs et al. |
| 6,081,738 | A | 6/2000 | Hinohara et al. |
| 6,086,534 | A | 7/2000 | Kesten |
| 6,090,041 | A | 7/2000 | Clark et al. |
| 6,093,150 | A | 7/2000 | Chandler et al. |
| 6,109,270 | A | 8/2000 | Mah et al. |
| 6,135,968 | A | 10/2000 | Brounstein |
| 6,167,297 | A | 12/2000 | Benaron |
| 6,173,604 | B1 | 1/2001 | Xiang et al. |
| 6,203,533 | B1 | 3/2001 | Ouchi |
| 6,233,479 | B1 | 5/2001 | Haddad et al. |
| 6,258,576 | B1 | 7/2001 | Richards-Kortum et al. |
| 6,280,704 | B1 | 8/2001 | Schutt et al. |
| 6,287,302 | B1 | 9/2001 | Berube |
| 6,308,097 | B1 | 10/2001 | Pearlman |
| 6,315,981 | B1 | 11/2001 | Unger |
| 6,321,106 | B1 | 11/2001 | Lemelson |
| 6,331,166 | B1 | 12/2001 | Burbank et al. |
| 6,370,426 | B1 | 4/2002 | Campbell et al. |
| 6,375,634 | B1 | 4/2002 | Carroll |
| 6,377,841 | B1 | 4/2002 | Lin et al. |
| 6,380,747 | B1 | 4/2002 | Goldfine et al. |
| 6,397,095 | B1 | 5/2002 | Eyuboglu et al. |
| 6,405,733 | B1 | 6/2002 | Fogarty et al. |
| 6,411,103 | B1 | 6/2002 | Tobais et al. |
| 6,500,112 | B1 | 12/2002 | Khouri |
| 6,530,944 | B2 | 3/2003 | West et al. |
| 6,544,185 | B2 | 4/2003 | Montegrande |
| 6,546,787 | B1 | 4/2003 | Schiller et al. |
| 6,564,806 | B1 | 5/2003 | Fogarty et al. |
| 6,592,520 | B1 | 7/2003 | Peszynski et al. |
| 6,597,185 | B1 | 7/2003 | Talanov et al. |
| 6,671,540 | B1 | 12/2003 | Hochman |
| 6,677,755 | B2 | 1/2004 | Belt et al. |
| 6,695,782 | B2 | 2/2004 | Ranucci et al. |
| 6,699,206 | B2 | 3/2004 | Burbank et al. |
| 6,722,371 | B1 | 4/2004 | Fogarty et al. |
| 6,728,565 | B2 | 4/2004 | Wendlandt |
| 6,741,077 | B2 | 5/2004 | Yokoyama et al. |
| 6,747,454 | B2 | 6/2004 | Belt |
| 6,752,154 | B2 | 6/2004 | Fogarty et al. |
| 6,766,185 | B2 | 7/2004 | Scott |
| 6,813,515 | B2 | 11/2004 | Hashimshony |
| 6,064,081 | A1 | 1/2005 | Hashimshony |
| 6,840,948 | B2 | 1/2005 | Albrecht et al. |
| 6,909,084 | B2 | 6/2005 | Tachi et al. |
| 6,936,003 | B2 | 8/2005 | Iddan |
| 6,962,587 | B2 | 11/2005 | Johnson et al. |
| 7,082,325 | B2 | 7/2006 | Hashimshony et al. |
| 7,184,824 | B2 | 2/2007 | Hashimshony |
| 2001/0051774 | A1 | 12/2001 | Littrup et al. |
| 2002/0055754 | A1 | 5/2002 | Ranucci et al. |
| 2002/0059938 | A1 | 5/2002 | Fogarty et al. |
| 2002/0068880 | A1 | 6/2002 | Burbank et al. |
| 2002/0072676 | A1 | 6/2002 | Afanassicva |
| 2002/0120265 | A1 | 8/2002 | Fowler |
| 2002/0148277 | A1 | 10/2002 | Umeda |
| 2003/0036674 | A1 | 2/2003 | Bouton |
| 2003/0045798 | A1 | 3/2003 | Hular et al. |
| 2003/0062897 | A1 | 4/2003 | Belt et al. |
| 2003/0117140 | A1 | 6/2003 | Belt et al. |
| 2003/0138378 | A1 | 7/2003 | Hashimshony |
| 2003/0146814 | A1 | 8/2003 | Wiltshire |
| 2003/0163037 | A1 | 8/2003 | Bladen et al. |
| 2003/0171664 | A1 | 9/2003 | Wendlandt |
| 2003/0187347 | A1 | 10/2003 | Nevo et al. |
| 2003/0187366 | A1 | 10/2003 | Hashimshony |
| 2003/0199753 | A1 | 10/2003 | Hibner et al. |
| 2003/0216648 | A1 | 11/2003 | Lizzi et al. |
| 2003/0229343 | A1 | 12/2003 | Albrecht et al. |
| 2004/0065158 | A1 | 4/2004 | Schrepfer et al. |
| 2004/0168692 | A1 | 9/2004 | Fogarty et al. |
| 2004/0254457 | A1 | 12/2004 | Van der Weide |
| 2005/0010131 | A1 | 1/2005 | Burbank et al. |
| 2005/0021019 | A1 | 1/2005 | Hashimshony et al. |
| 2005/0107717 | A1 | 5/2005 | Yamamoto et al. |
| 2005/0119648 | A1 | 6/2005 | Swanson |
| 2005/0159689 | A1 | 7/2005 | Olson |
| 2006/0253107 | A1 | 11/2006 | Hashimshony et al. |
| 2006/0264738 | A1 | 11/2006 | Hashimshony et al. |
| 2007/0032739 | A1 | 2/2007 | Hashimshony et al. |
| 2007/0032747 | A1 | 2/2007 | Hashimshony et al. |
| 2007/0092059 | A1 | 4/2007 | Eberhard et al. |
| 2007/0179397 | A1 | 8/2007 | Hashimshony et al. |
| 2007/0255169 | A1 | 11/2007 | Hashimshony et al. |
| 2007/0260156 | A1 | 11/2007 | Hashimshony |

| | | | |
|---|---|---|---|
| 2008/0021343 | A1 | 1/2008 | Hashimshony et al. |
| 2008/0039742 | A1 | 2/2008 | Hashimshony et al. |
| 2008/0154090 | A1 | 6/2008 | Hashimshony |
| 2008/0287750 | A1 | 11/2008 | Hashimshony et al. |
| 2009/0062637 | A1 | 3/2009 | Hashimshony et al. |

FOREIGN PATENT DOCUMENTS

| | | |
|---|---|---|
| DE | 19705260 A1 | 8/1997 |
| DE | 19734978 A1 | 2/1999 |
| EP | 419235 | 3/1991 |
| GB | 01153980 | 3/1968 |
| JP | 2003-516214 | 5/2003 |
| WO | WO 97/12553 | 4/1997 |
| WO | WO 01/42807 | 6/2001 |
| WO | WO 01/43630 | 6/2001 |
| WO | WO 01/65240 | 7/2001 |
| WO | WO 02/32335 | 4/2002 |
| WO | WO 02/058531 | 8/2002 |
| WO | WO 03/009752 | 2/2003 |
| WO | WO 03/060462 | 7/2003 |
| WO | WO 2005/009200 | 3/2005 |
| WO | WO 2005/089065 | 9/2005 |
| WO | WO 2006/072947 | 7/2006 |
| WO | WO 2006/092797 | 9/2006 |
| WO | WO 2006/103665 | 10/2006 |
| WO | WO 2007/015255 | 2/2007 |
| WO | WO 2007/083310 | 7/2007 |
| WO | WO 2008/132714 | 11/2008 |
| WO | WO 2008/132750 | 11/2008 |

OTHER PUBLICATIONS

Translation of Notice of Reason for Rejection Dated Aug. 24, 2010 From the Japanese Patent Office Re. Application No. 2006-520980.
Communication Pursuant to Article 94(3) EPC Dated Oct. 7, 2009 From the European Patent Office Re.: Application No. 06728196.4.
International Preliminary Report on Patentability Dated Nov. 12, 2009 From the International Bureau of WIPO Re.: Application No. PCT/IL2008/000406.
Official Action Dated Aug. 27, 2009 From the US Patent and Trademark Office Re.: U.S. Appl. No. 11/705,143.
Official Action Dated Oct. 27, 2009 From the US Patent and Trademark Office Re.: U.S. Appl. No. 11/487,431.
Official Action Dated Aug. 31, 2009 From the US Patent and Trademark Office Re.: U.S. Appl. No. 11/797,166.
Response Dated Oct. 13, 2009 to Official Action of Sep. 15, 2009 From the US Patent and Trademark Office Re.: U.S. Appl. No. 11/196,732.
Response Dated Oct. 13, 2009 to Official Action of Dec. 18, 2008 From the US Patent and Trademark Office Re.: U.S. Appl. No. 10/534,544.
Response Dated Nov. 25, 2009 to Official Action of Aug. 27, 2009 From the US Patent and Trademark Office Re.: U.S. Appl. No. 11/705,143.
Supplementary Partial European Search Report and the European Searching Opinion Dated Dec. 4, 2009 From the European Patent Office Re.: Application No. 06700052.1.
Translation of Office Action Dated Sep. 18, 2009 From the State Intellectual Property Office of the People's Republic of China Re.: Application No. 200680006513.7.
Translation of Notification to Grant Patent Right for Invention Dated Aug. 3, 2010 From the State Intellectual Property Office of the People's Republic of China Re.: Application No. 200680019026.4.
Response Dated Sep. 2, 2010 to Communication Pursuant to Article 94(3) EPC of Mar. 15, 2010 From the European Patent Office Re.: Application No. 06700052.1.
Response Dated Aug. 30, 2010 to Official Action of Mar. 11, 2010 From the US Patent and Trademark Office Re.: U.S. Appl. No. 11/797,166.
Communication Pursuant to Article 96(2) EPC Dated Aug. 10, 2006 From the European Patent Office Re.: Application No. 02795418.9
Communication Pursuant to Article 96(2) EPC Dated Jan. 12, 2006 From the European Patent Office Re.: Application No. 02795418.9.
Communication Relating to the Results of the Partial International Search Dated Sep. 1, 2008 From the International Searching Authority Re.: Application No. PCT/IL2008/000406.

Examination Report Dated Nov. 18, 2008 From the Government of India, Patent Office Re.: Application No. 668/CHENP/2006.
International Preliminary Report on Patentability Dated Feb. 4, 2008 From the International Preliminary Examining Authority Re.: Application No. PCT/IL06/00392.
International Preliminary Report on Patentability Dated Jan. 22, 2009 From the International Bureau of WIPO Re.: Application No. PCT/IL2006/000908.
International Preliminary Report on Patentability Dated Apr. 26, 2007 From the International Bureau of WIPO Re.: Application No. PCT/IL2005/000330.
International Preliminary Report on Patentability Dated Aug. 9, 2007 From the International Bureau of WIPO Re.: Application No. PCT/IL2006/000015.
International Search Report Dated Nov. 27, 2008 From the International Searching Authority Re.: Application No. PCT/IL2008/000406.
Office Action Dated Feb. 11, 2009 From the Israeli Patent Office Re.: Application No. 173231 and Its Translation Into English.
Office Action Dated Nov. 18, 2008 From the Government of India, Patent Office Re.: Application No. 668/CHENP/2006.
Office Action Dated Mar. 20, 2009 From the State Intellectual Property Office of the People's Republic of China Re.: Application No. 200680019026.4.
Official Action Dated Apr. 1, 2008 From US Patent and Trademark Office Re.: U.S. Appl. No. 11/745,334.
Official Action Dated Jun. 3, 2005 From the US Patent and Trademark Office Re.: U.S. Appl. No. 10/891,750.
Official Action Dated Jun. 4, 2007 From the US Patent and Trademark Office Re.: U.S. Appl. No. 10/298,196.
Official Action Dated Jul. 9, 2008 From the US Patent and Trademark Office Re.: U.S. Appl. No. 11/196,732.
Official Action Dated Apr. 10, 2006 From the US Patent and Trademark Office Re.: U.S. Appl. No. 10/965,752.
Official Action Dated Feb. 10, 2006 From the US Patent and Trademark Office Re.: U.S. Appl. No. 10/298,196.
Official Action Dated Oct. 10, 2006 From the US Patent and Trademark Office Re.: U.S. Appl. No. 10/298,196.
Official Action Dated Nov. 19, 2007 From the US Patent and Trademark Office Re.: U.S. Appl. No. 11/196,732.
Official Action Dated Mar. 21, 2008 From the US Patent and Trademark Office Re.: U.S. Appl. No. 10/558,831.
Official Action Dated Jan. 24, 2008 From the US Patent and Trademark Office Re.: U.S. Appl. No. 10/298,196.
Response Dated Aug. 3, 2007 to Written Opinion of May 3, 2007 From the International Searching Authority Re.: Application No. PCT/IL06/00392.
Response Dated Jan. 4, 2007 to Communication Pursuant to Article 96(2) of Aug. 10, 2006 From the European Patent Office Re.: Application No. 02795418.9.
Response Dated Mar. 16, 2007 to Communication Pursuant to Article 96(2) EPC of Jan. 19, 2007 From the European Patent Office Re.: Application No. 02795418.9.
Supplementary European Search Report and the European Search Opinion Dated Jun. 5, 2009 From the European Patent Office Re.: Application No. 06728196.4.
Translation of the Notice of Reason for Rejection Dated Oct. 31, 2008 From the Japanese Patent Office Re.: Application No. 2003-560509.
Written Opinion Dated Nov. 27, 2008 From the International Searching Authority Re.: Application No. PCT/IL2008/000406.
Communication Pursuant to Article 94(3) EPC Dated Mar. 15, 2010 From the European Patent Office Re.: Application No. 06700052.1.
Notice of Allowance Dated Oct. 20, 2006 From the US Patent and Trademark Office Re.: U.S. Appl. No. 10/965,752.
Official Action Dated Feb. 4, 2010 From the US Patent and Trademark Office Re.: U.S. Appl. No. 11/196,732.
Official Action Dated Mar. 11, 2010 From the US Patent and Trademark Office Re.: U.S. Appl. No. 11/797,166.
Official Action Dated Mar. 16, 2010 From the US Patent and Trademark Office Re.: U.S. Appl. No. 11/887,571.
Official Action Dated Mar. 17, 1010 From the US Patent and Trademark Office Re.: U.S. Appl. No. 10/567,581.

Official Action Dated Aug. 27, 2009 From the US Patent and Trademark Office Re.: U.S. Appl. No. 11/797,167.
Reponse Dated Mar. 1, 2010 to Official Action of Oct. 27, 2009 From the US Patent and Trademark Office Re.: U.S. Appl. No. 11/487,431.
Response Dated Jan. 3, 2010 to Office Action of Sep. 18, 2009 From the State Intellectual Property Office of the People's Republic of China Re.: Application No. 200680006513.7.
Response Dated Feb. 8, 2010 to Communication Pursuant to Article 94(3) EPC of Oct. 7, 2009 From the European Patent Office Re.: Application No. 06728196.4.
Response Dated Nov. 25, 2009 to Official Action of Aug. 27, 2009 From the US Patent and Trademark Office Re.: U.S. Appl. No. 11/705,143.
Response Dated Dec. 30, 2009 to Official Action of Aug. 31, 2009 From the US Patent and Trademark Office Re.: U.S. Appl. No. 11/797,166.
Rajshekhar "Continuous Impedence Monitoring During CT-Guided Stereotactic Surgery: Relative Value in Cystic and Solid Lesions", British Journal of Neurosurgery, 6: 439-444, 1992.
Misra et al. "Noninvasive Electrical Characterization of Materials at Microwave Frequencies Using An Open-Ended Coaxial Line: Test of An Improved Calibration Technique", IEEE Transactions on Microwave Theory & Techniques, 38(1): 8-13, 1990.
Burdette et al. "In Vivo Probe Measurement Technique for Determining Dielectric Properties at VFW Through Microwave Frequencies", IEEE Transactions on Microwave Theory & Techniques, MTT-28(4): 414-427, 1980.
Xu et al. "Measurement of Microwave Permittivity Using Open Ended Elliptical Coaxial Probes", IEEE Transactions on Microwave Theory & Techniques, 40(1): 143-150, 1992.
Stuchly et al. "Measurement of Radio Frequency Permittivity of Biological Tissues With An Open-Ended Coaxial Line: Part II-Experimental Results", IEEE Transactions on Microwave Theory & Techniques, MTT-30(1): 87-91, 1982.
Mosig et al. "Reflection of An Open-Ended Coaxial Line", IEEE Transactions on Instrumentation & Measurement, IM-30(1): 46-51, 1981.
Brown "A Survey of Image Registration Techniques", ACM Computing Surveys, 24(4): 325-376, 1992.
Smith et al. "In Vivo Measurement of Tumor Conductiveness With the Magnetic Bioimpedance Method", IEEE Transactions on Biomedical Engineering, 47(10): 1403-1405, 2000.
Schwan "Mechanism Responsible for Electrical Properties of Tissues and Cell Suspensions", Medical Process Through Technology, 19: 163-165, 1993.
Surowiec et al. "Dielectric Properties of Breast Carcinoma and the Surrounding Tissues", IEEE Transactions on Biomedical Engineering, 35(4): 257-263, 1988.
Official Action Dated Jul. 9, 2010 From the US Patent and Trademark Office Re.: U.S. Appl. No. 11/705,143.
Notice of Allowance Dated Jun. 29, 2010 From the US Patent and Trademark Office Re.: U.S. Appl. No. 11/487,431.
Response Dated Aug. 4, 2010 to Official Action of Feb. 4, 2010 From the US Patent and Trademark Office Re.: U.S. Appl. No. 11/196,732.
Translation of Notification to Grant Patent Right for Invention Dated Aug. 3, 2010 From the State Intellectual Property Office of the People's Republic of China Re.: Application No. 200680019026.4.
Examination Report Dated Feb. 1, 2008 From the Government of India, Patent Office Re.: Application No. 668/CHENP/2006.
International Search Report and the Written Opinion Dated May 3, 2007 From the International Searching Authority Re.: Application No. PCT/IL06/00392.
International Search Report and the Written Opinion Dated Feb. 5, 2007 From the International Searching Authority Re.: Application No. PCT/IL05/00330.
International Search Report and the Written Opinion Dated Jun. 22, 2005 From the International Searching Authority Re.: Application No. PCT/IL04/00641.
Response Dated Nov. 25, 2009 to Official Action of Aug. 27, 2009 From the US Patent and Trademark Office Re.: U.S. Appl. No. 11/797,167.
Supplementary European Search Report Dated Feb. 17, 2005 From the European Patent Office Re.: Application No. 02795418.9.
Translation of the Office Action Dated Jul. 27, 2007 From the Patent Office of the People's Republic of China Re.: Application No. 200480027097.X.
Official Action Dated Oct. 28, 2010 From the US Patent and Trademark Office Re.: U.S. Appl. No. 11/797,166.
Translation of Notice of Reason for Rejection Dated Feb. 15, 2011 From the Japanese Patent Office Re. Application No. 2006-520980.
Response Dated Sep. 16, 2010 to Official Action of Mar. 16, 2010 From the US Patent and Trademark Office Re.: U.S. Appl. No. 11/887,571.
Response Dated Sep. 29, 2010 to Official Action of Aug. 31, 2010 From the US Patent and Trademark Office Re. U.S. Appl. No. 11/350,102.
Response Dated Apr. 28, 2011 to Official Action of Oct. 28, 2010 From the US Patent and Trademark Office Re.: U.S. Appl. No. 11/797,166.
Communication Pursuant to Article 94(3) EPC Dated Sep. 27, 2010 From the European Patent Office Re.: Application No. 06728196.4.
Response Dated Sep. 16, 2010 to Official Action of Mar. 17, 2010 From the US Patent and Trademark Office Re.: U.S. Appl. No. 10/567,581.
Response Dated Mar. 28, 2011 to Communication Pursuant to Article 94(3) EPC of Sep. 27, 2010 From the European Patent Office Re.: Application No. 06728196.4.
Official Action Dated Dec. 8, 2010 From the US Patent and Trademark Office Re.: U.S. Appl. No. 11/196,732.
Official Action Dated Nov. 23, 2010 From the US Patent and Trademark Office Re.: U.S. Appl. No. 10/567,581.
Official Action Dated Jan. 6, 2011 From the US Patent and Trademark Office Re. U.S. Appl. No. 11/350,102.
Response Dated Dec. 27, 2010 to Official Action of Jul. 9, 2010 From the US Patent and Trademark Office Re.: U.S. Appl. No. 11/705,143.
Response Dated Jan. 16, 2011 to Notice of Reason for Rejection of Aug. 24, 2010 From the Japanese Patent Office Re. Application No. 2006-520980.
Communication Pursuant to Article 94(3) EPC Dated Feb. 1, 2011 From the European Patent Office Re.: Application No. 06700052.1.
Response Dated Jan. 26, 2011 to Office Action of Aug. 4, 2010 From the State Intellectual Property Office of the People's Republic of China Re. Application No. 200680037103.9.
Translation of Office Action Dated Aug. 4, 2010 From the State Intellectual Property Office of the People's Republic of China Re. Application No. 200680037103.9.
Notice of Allowance Dated May 17, 2011 From the US Patent and Trademark Office Re.: U.S. Appl. No. 11/705,143.

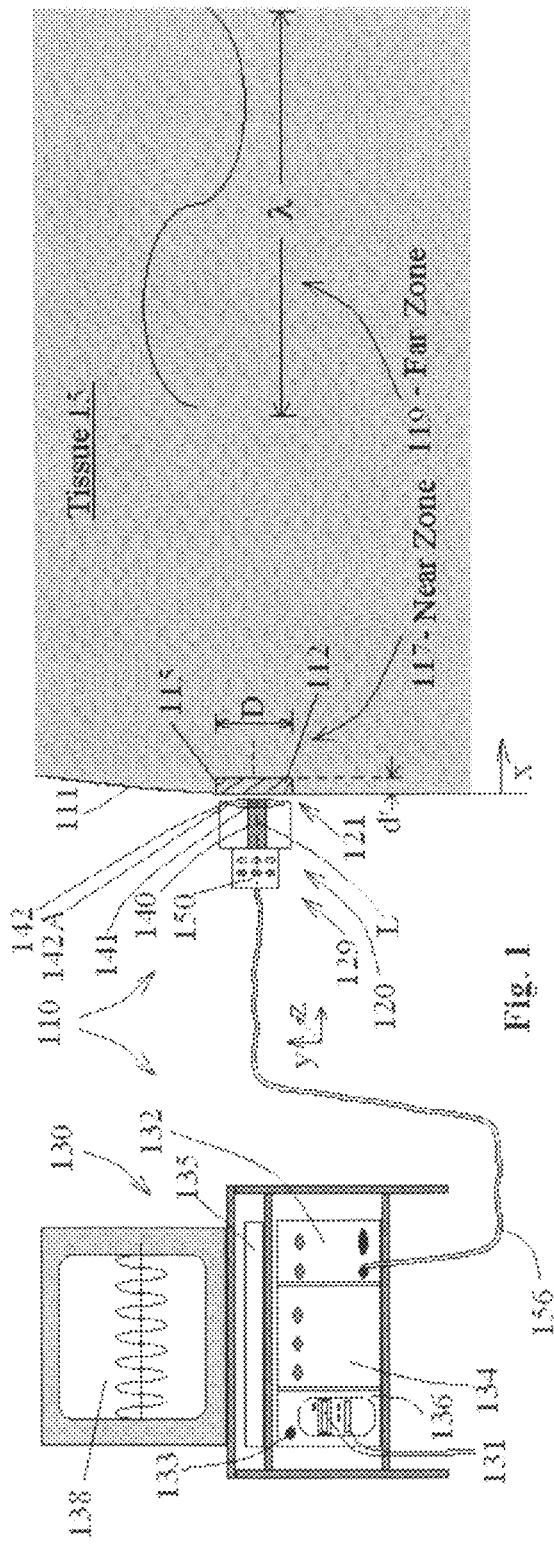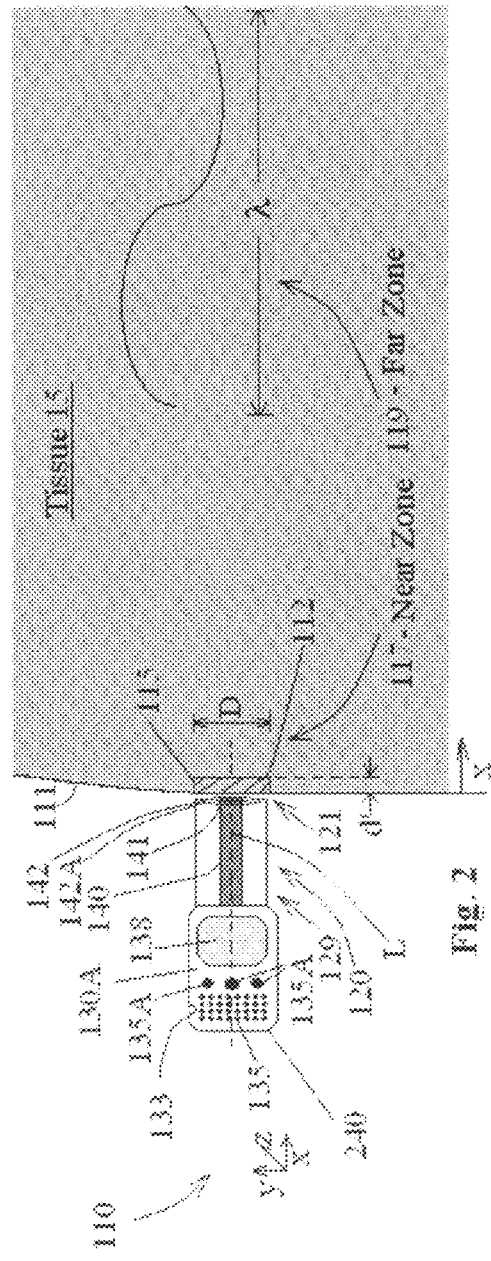

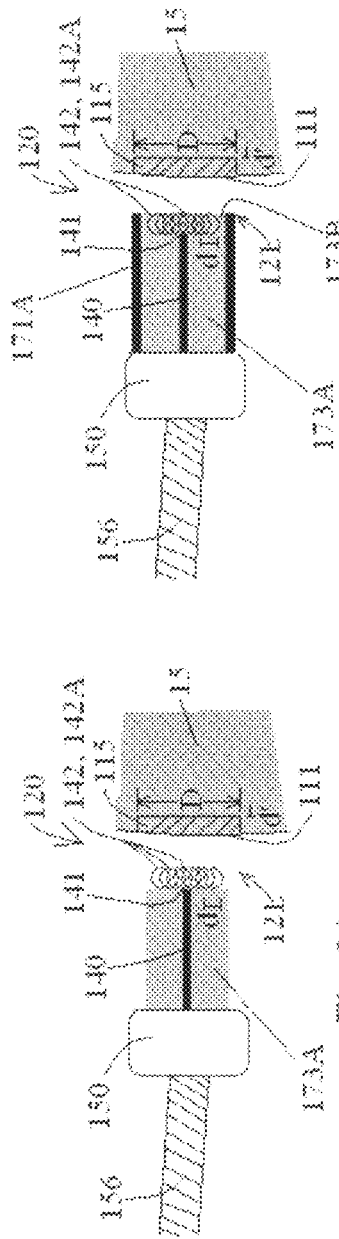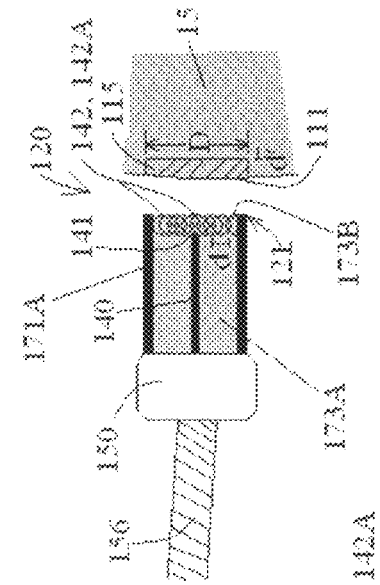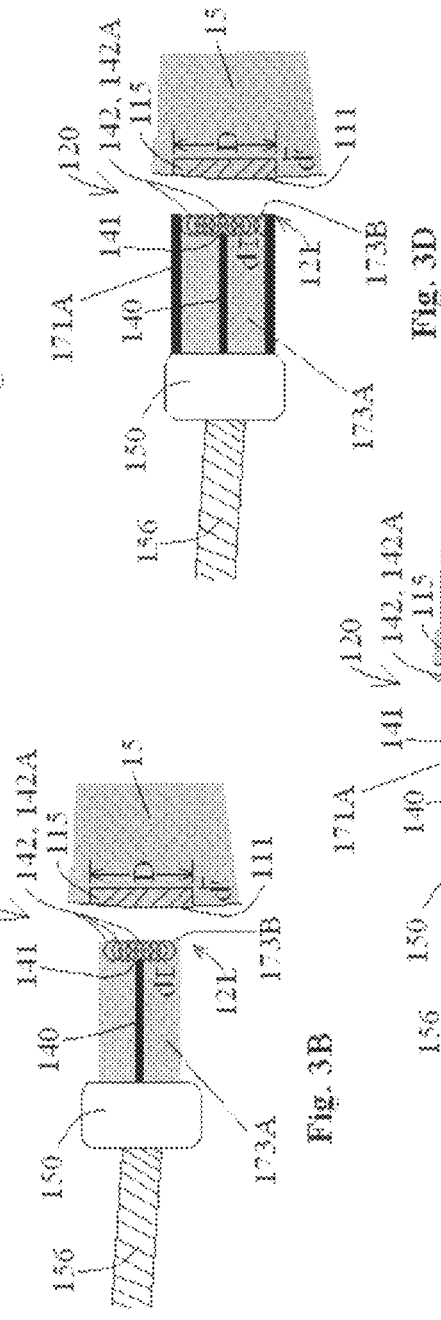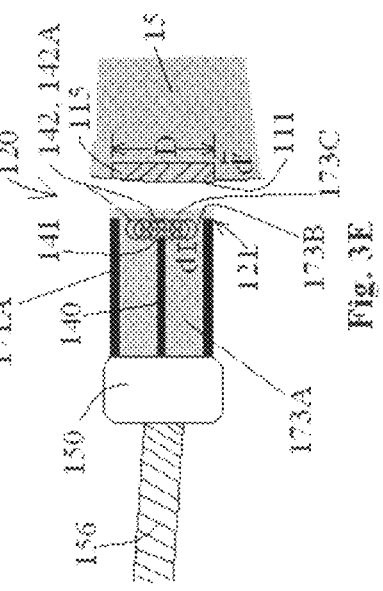

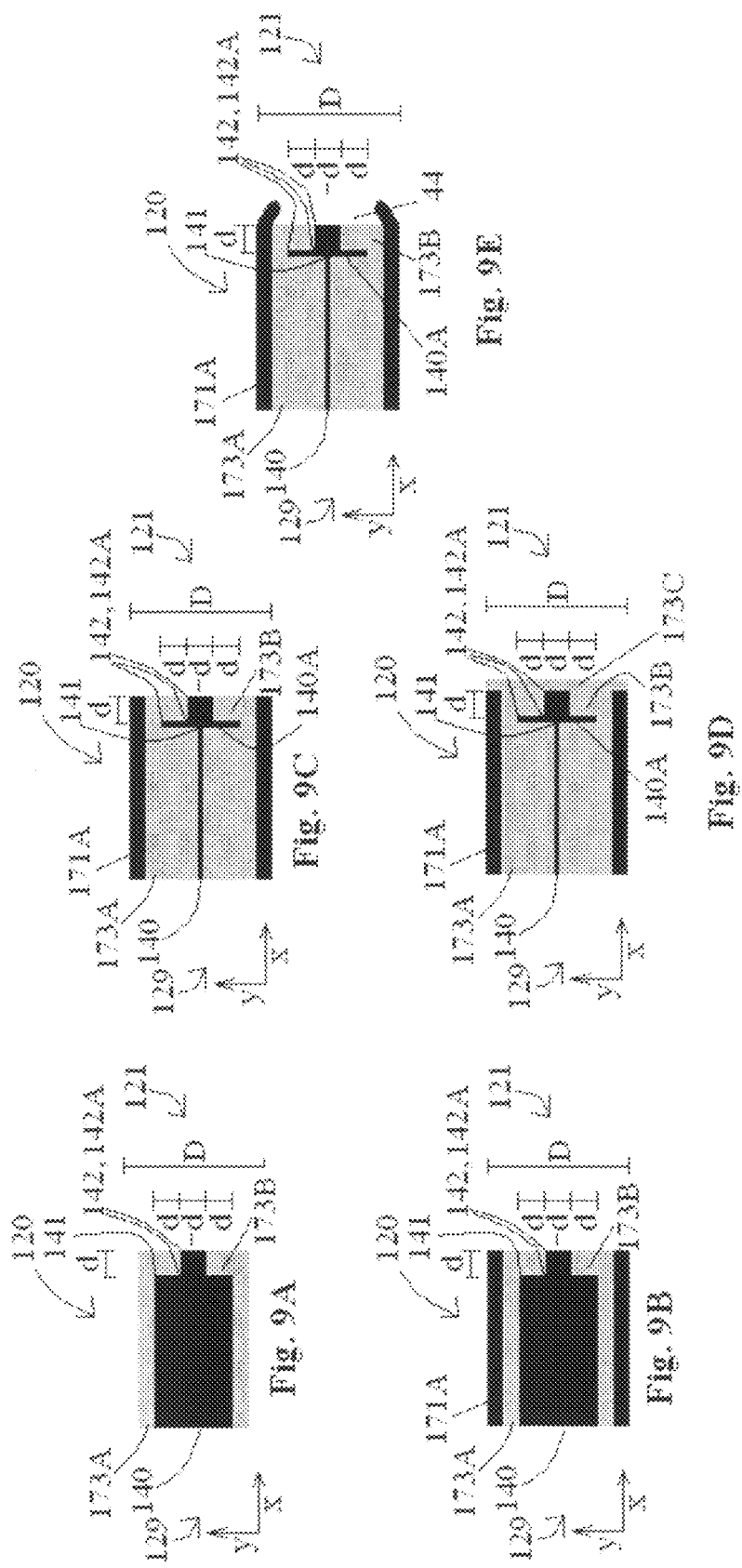

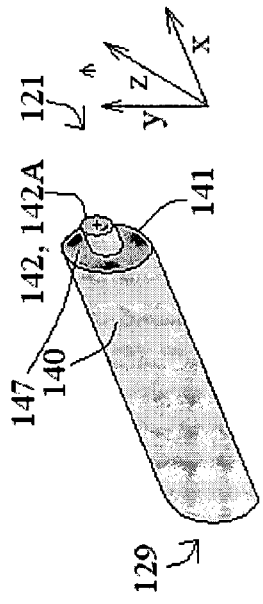
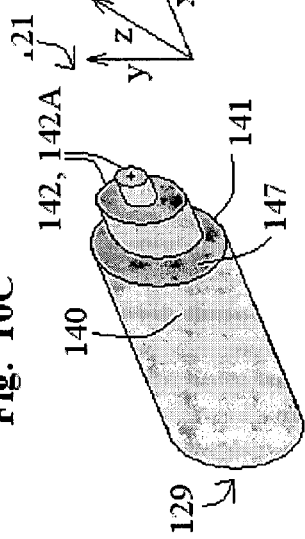
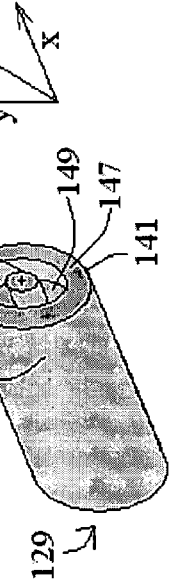
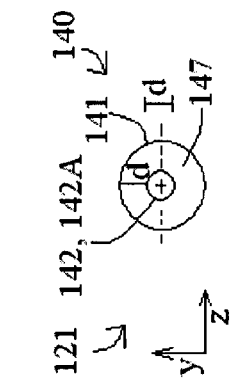
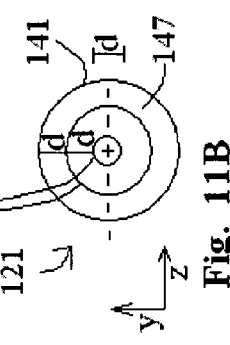
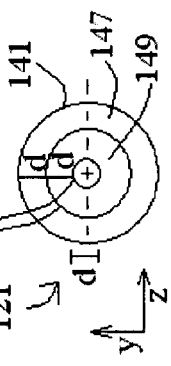
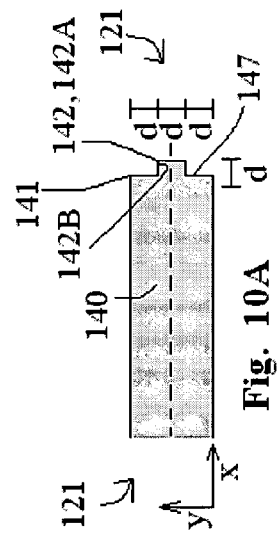
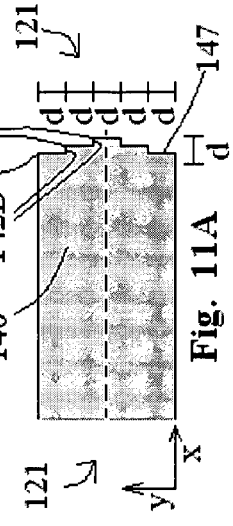
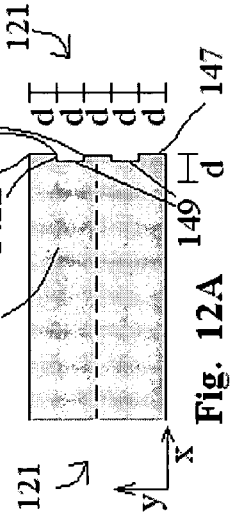

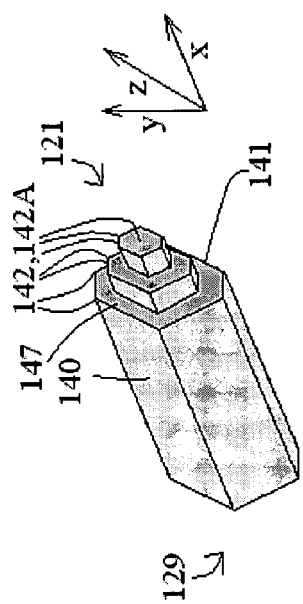
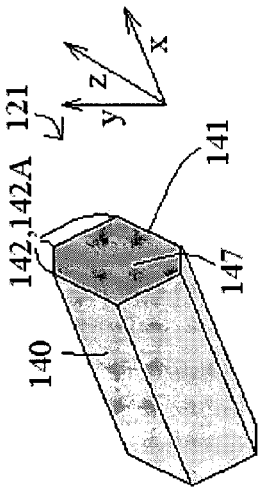
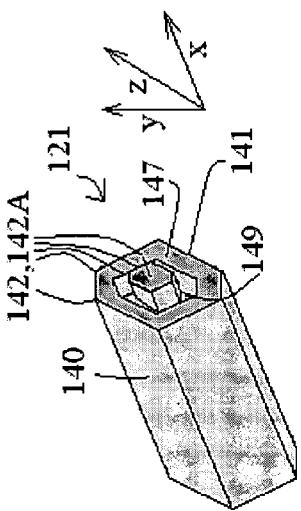
Fig. 13A  Fig. 13B  Fig. 13C
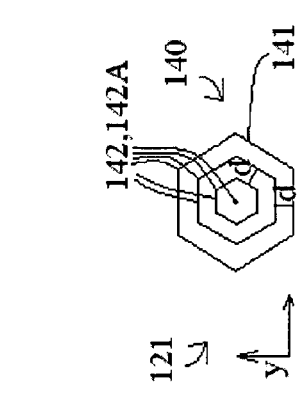
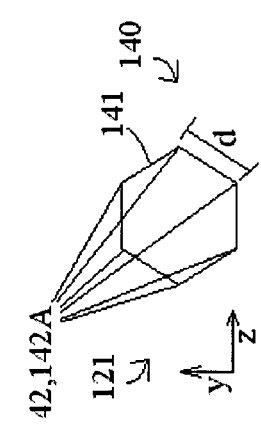
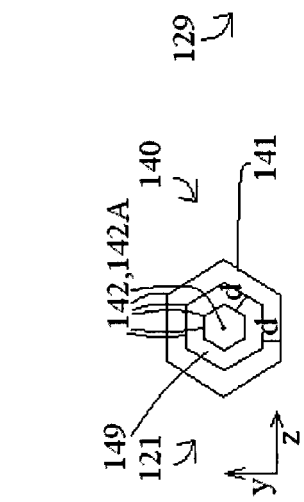
Fig. 14A  Fig. 14B  Fig. 14C
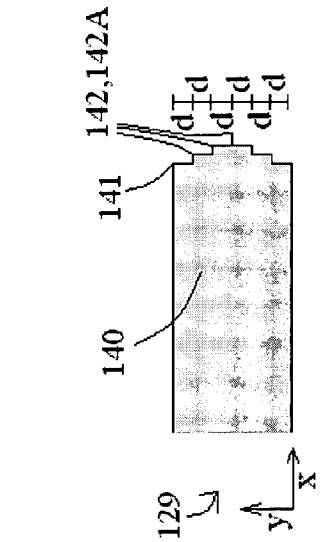
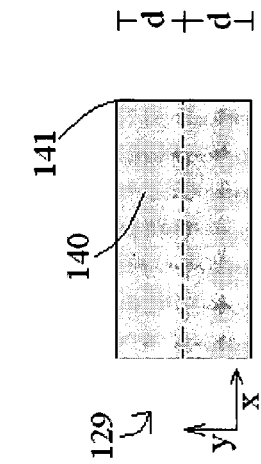
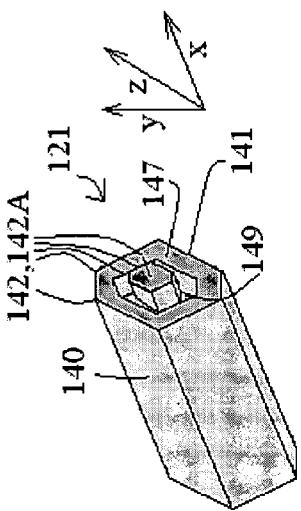
Fig. 15A  Fig. 15B  Fig. 15C

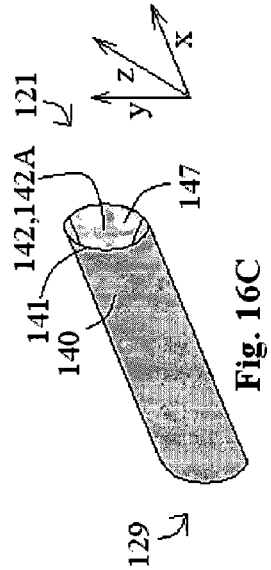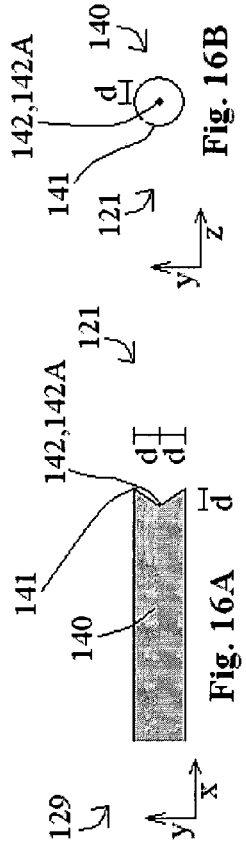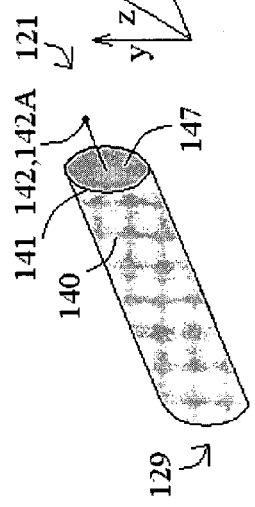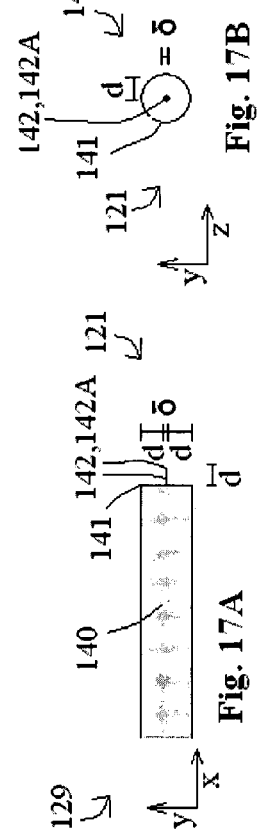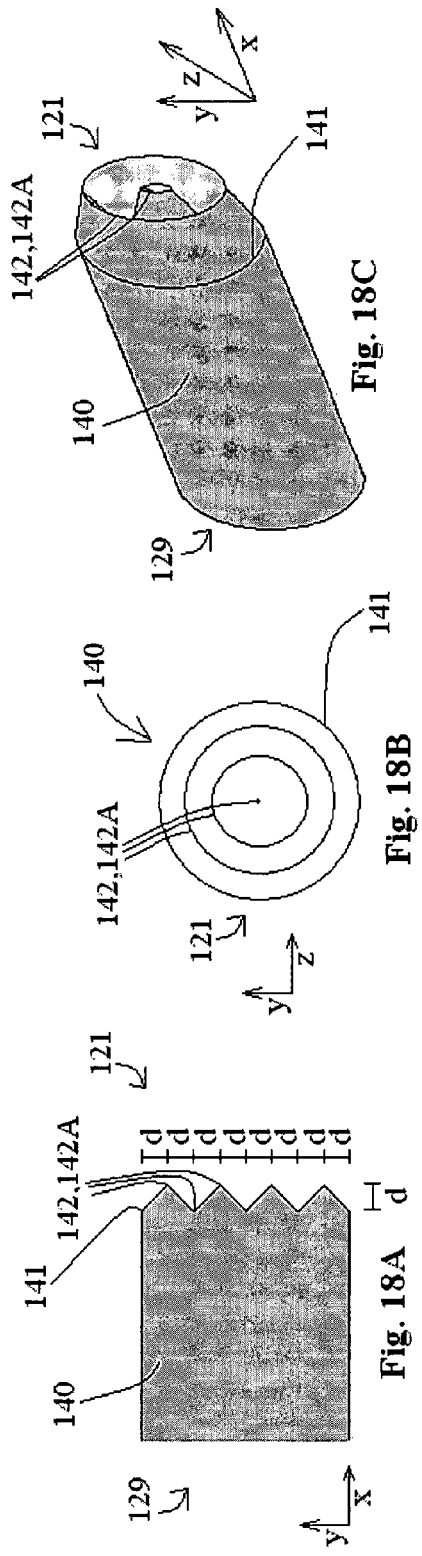

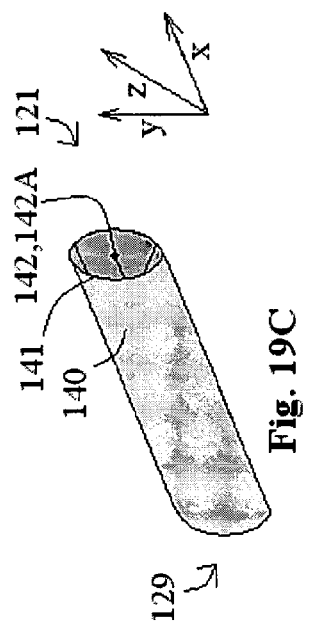
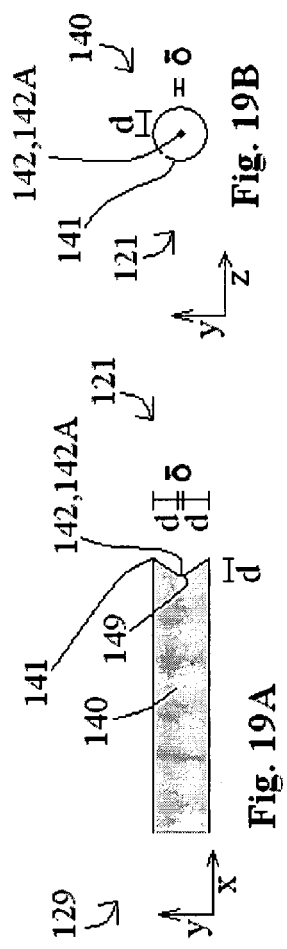
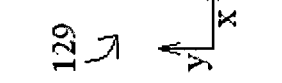

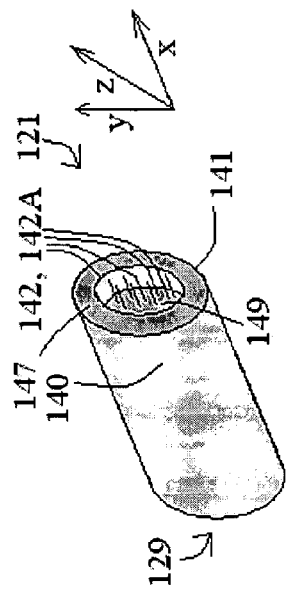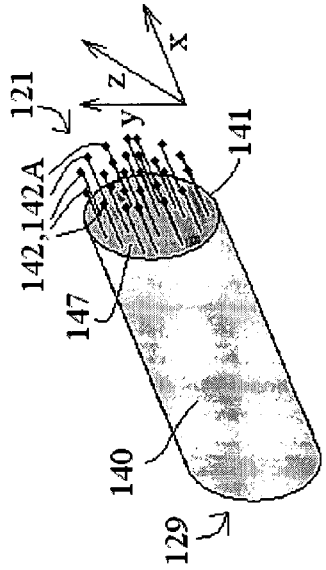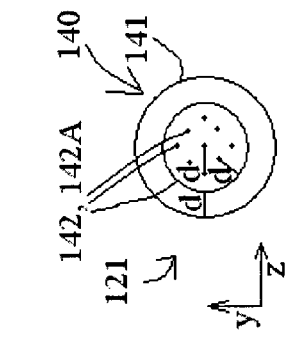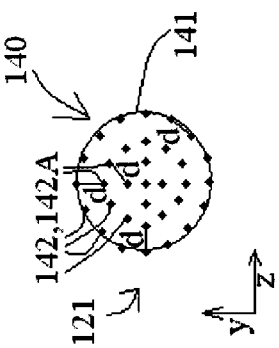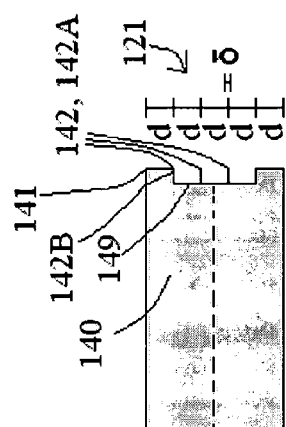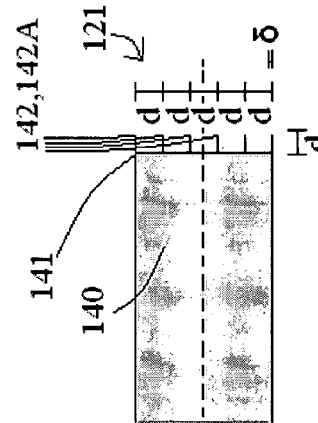

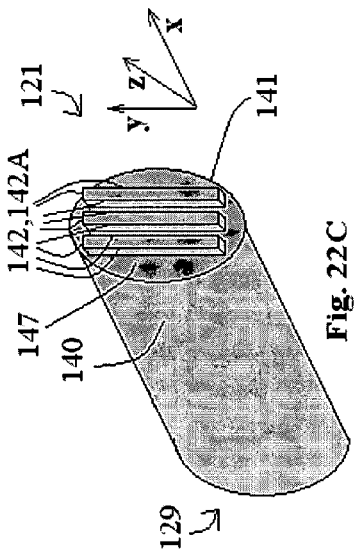
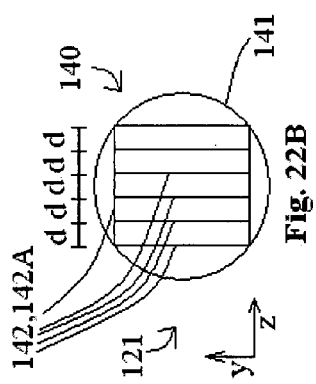
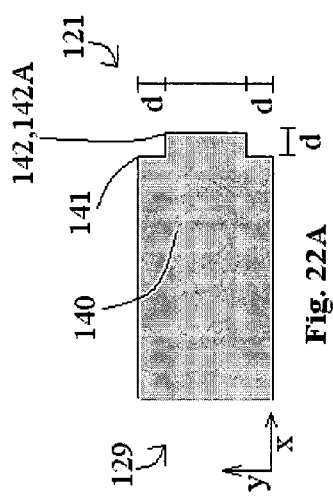
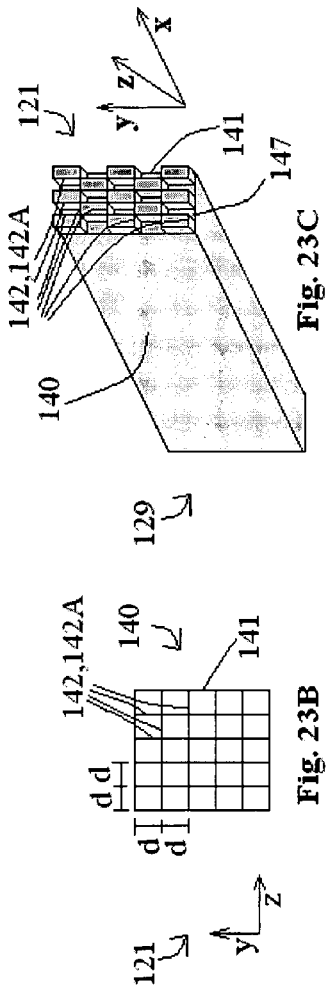
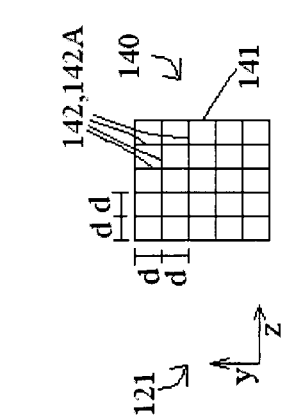
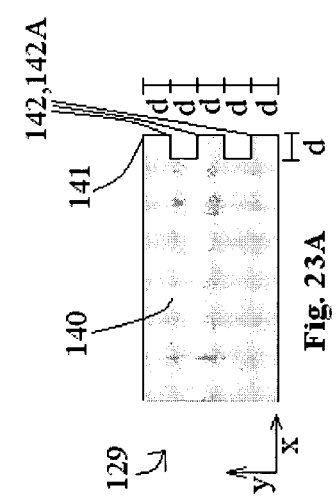
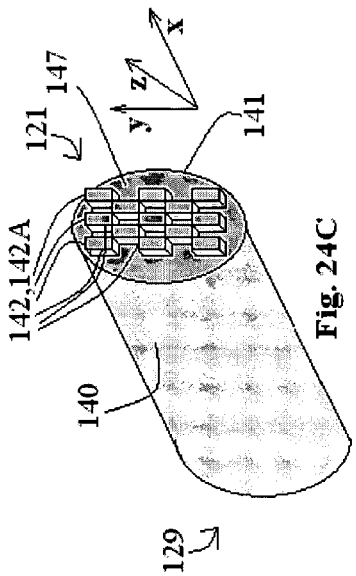
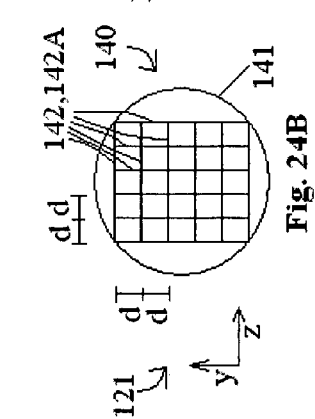
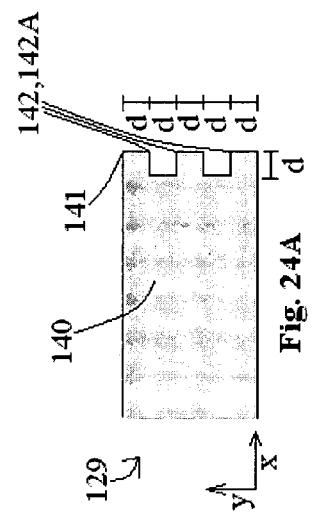

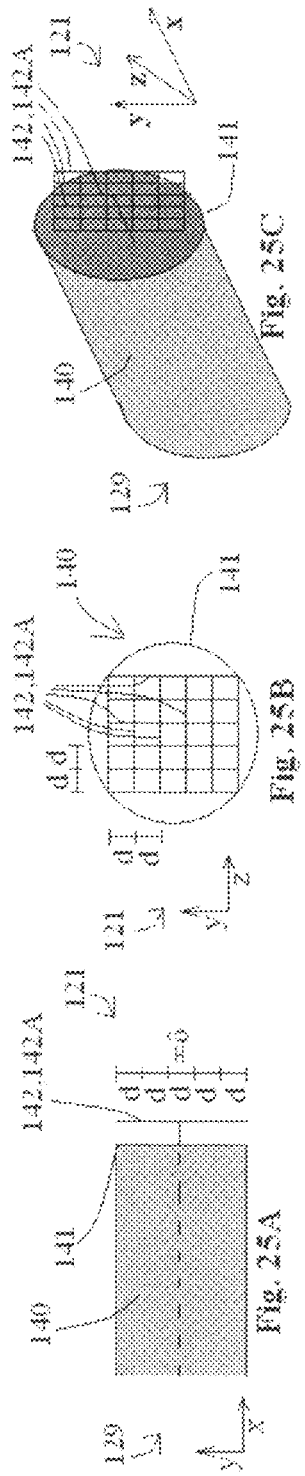
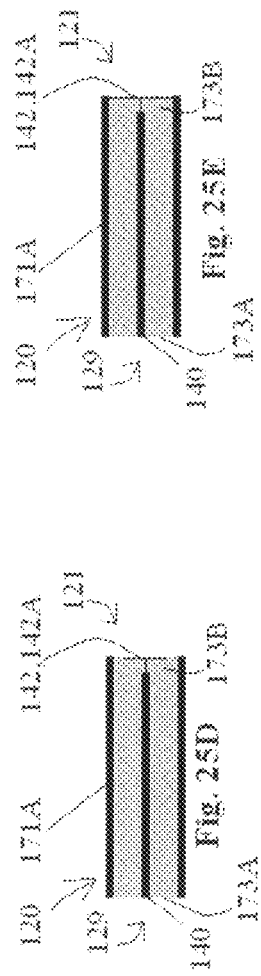
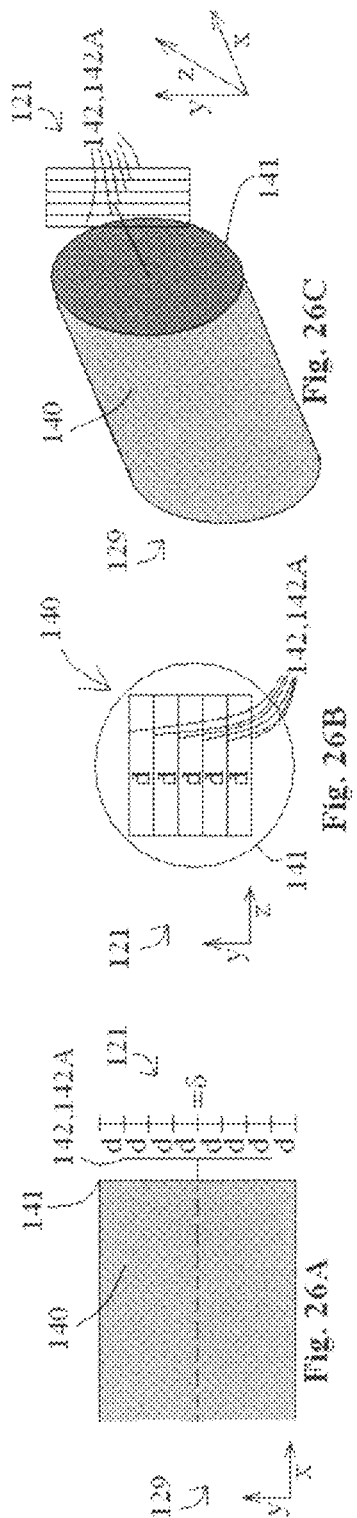

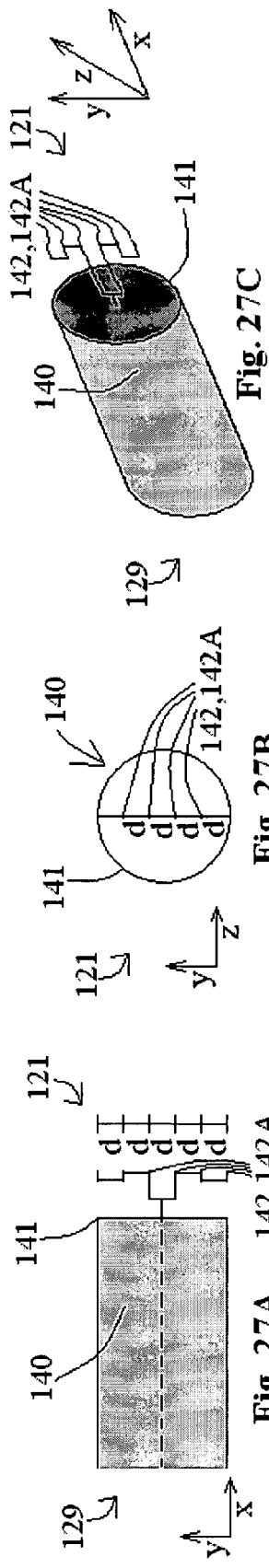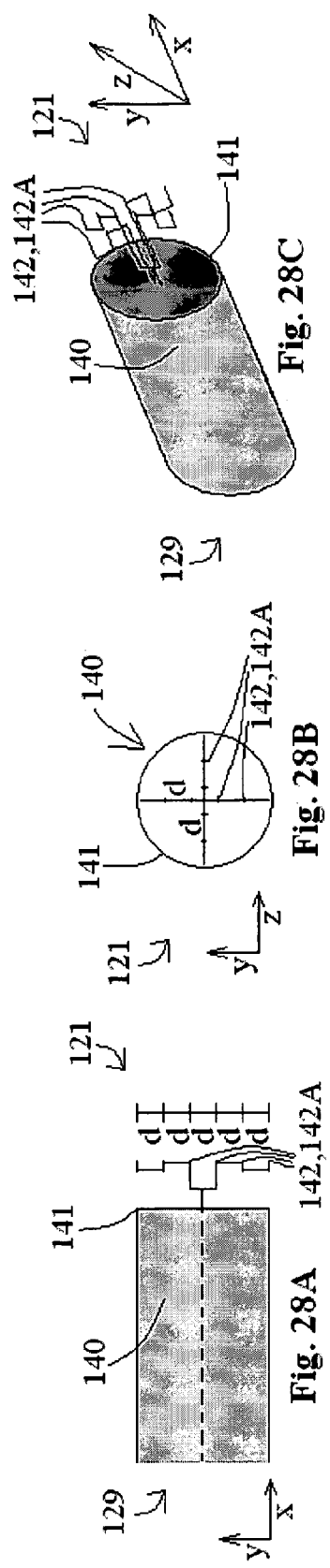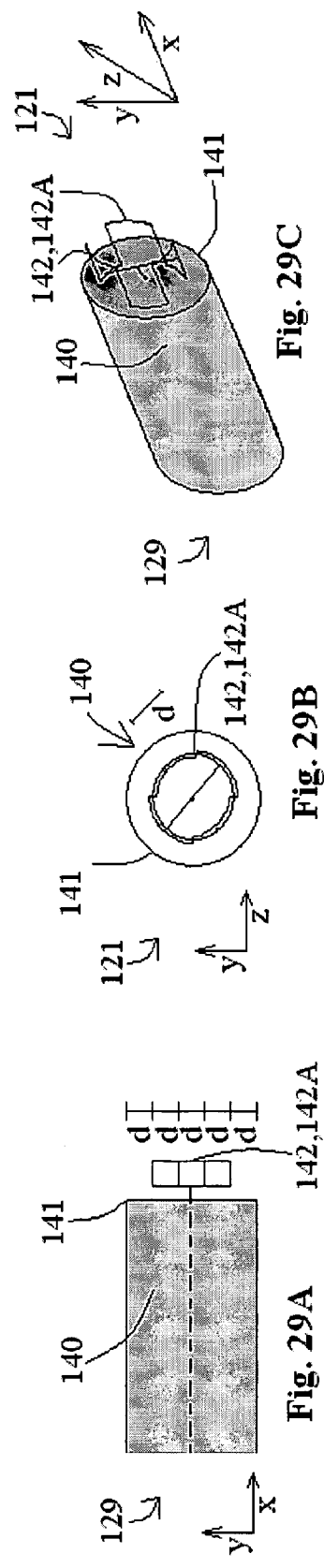

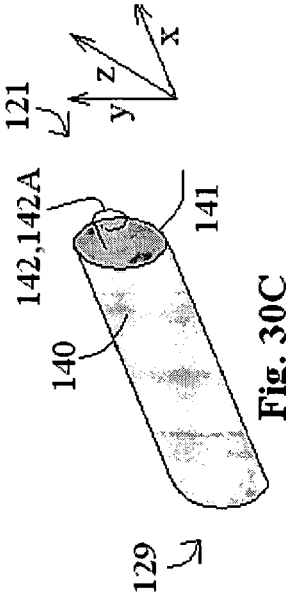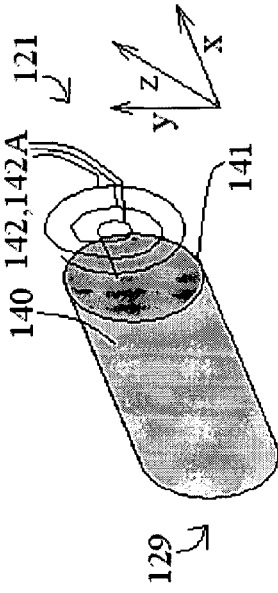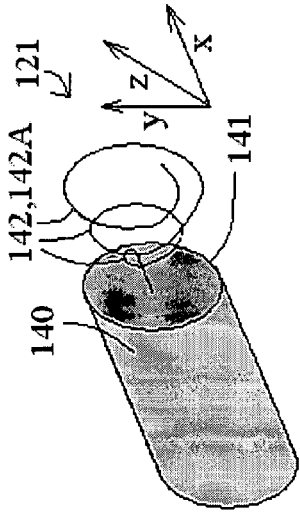
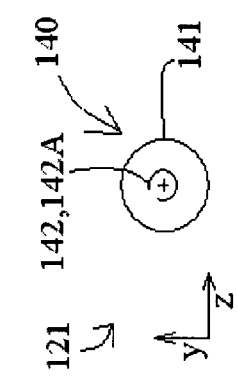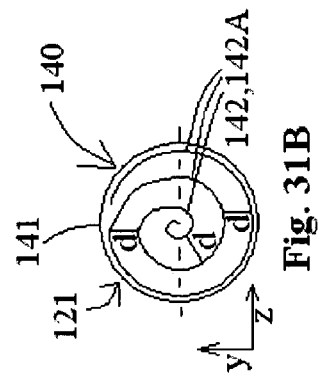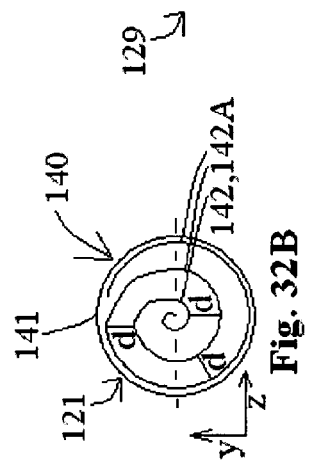
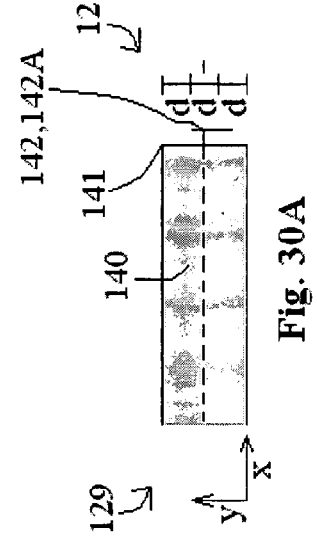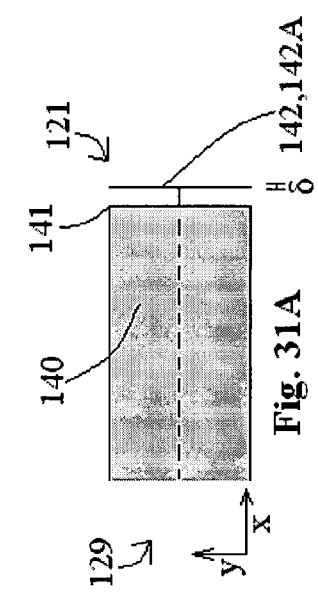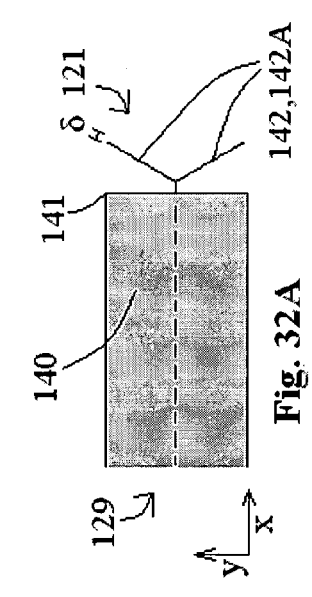

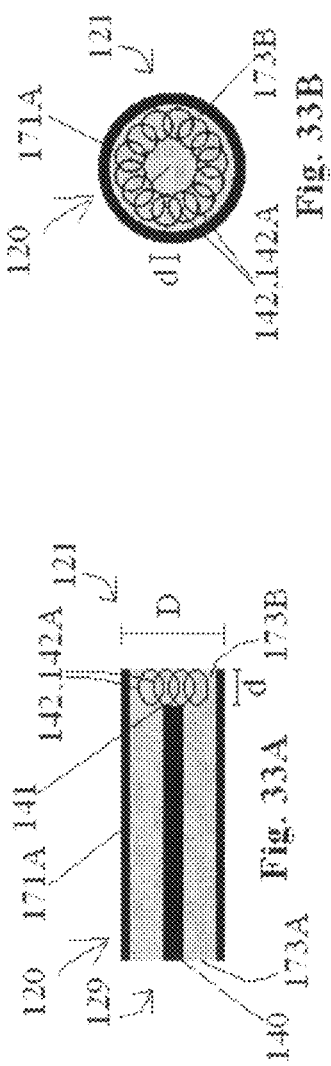
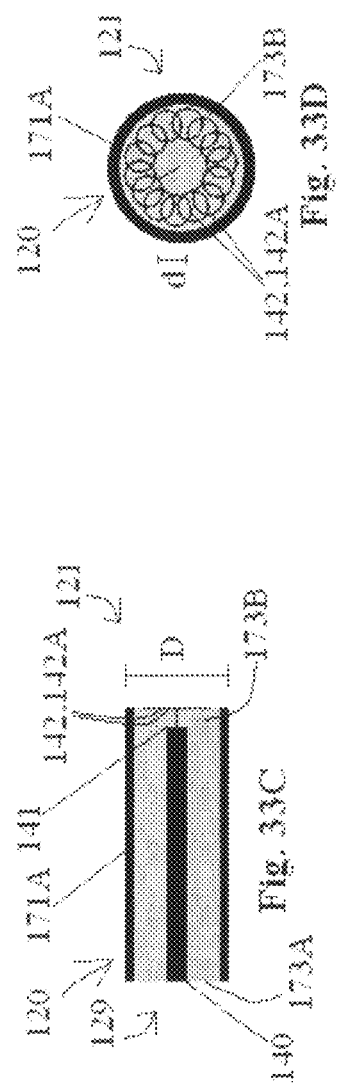
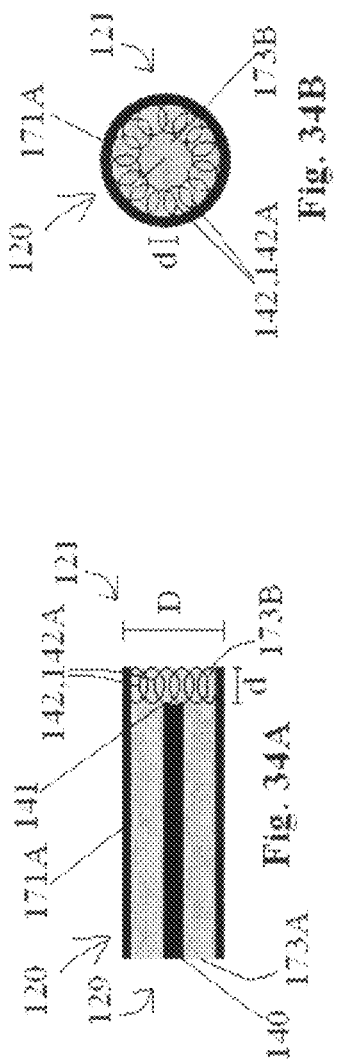

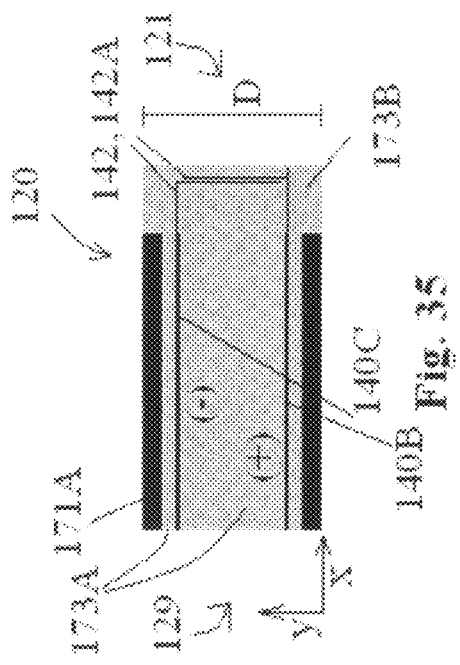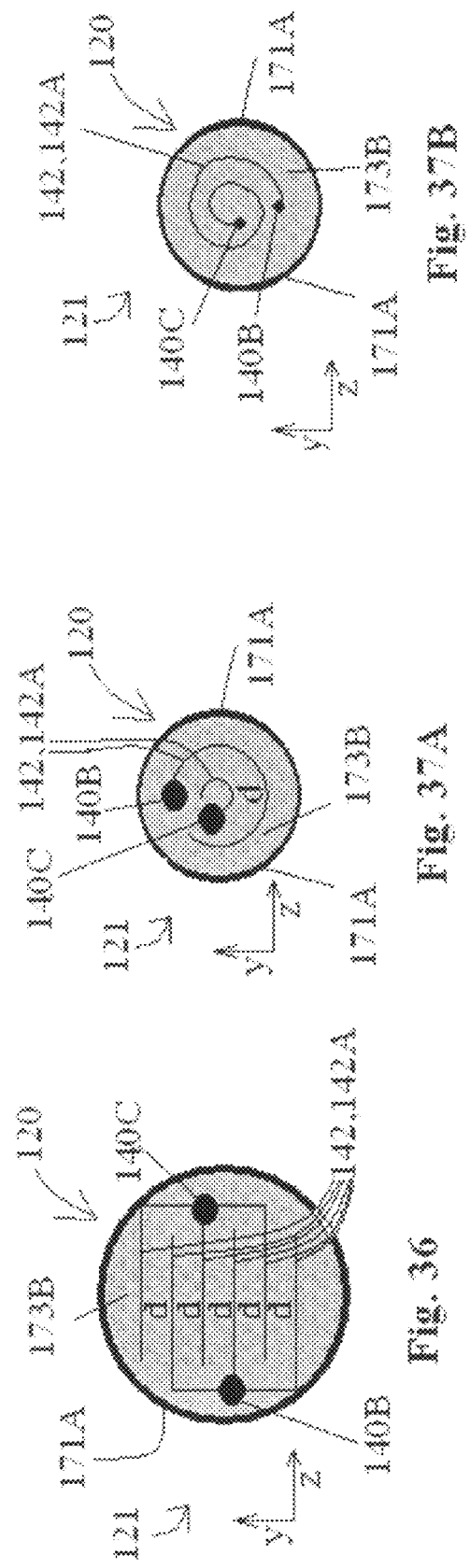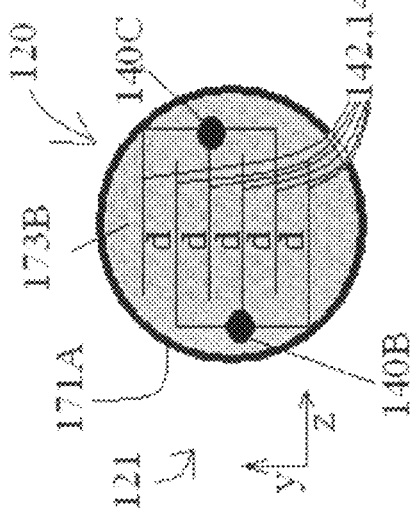

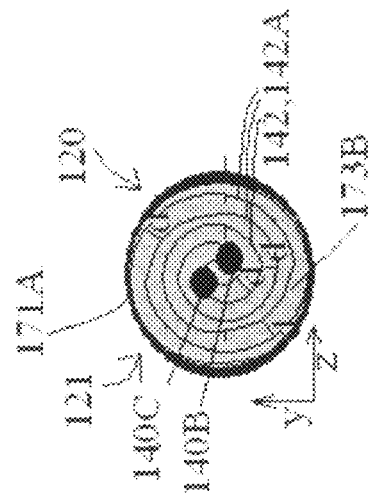
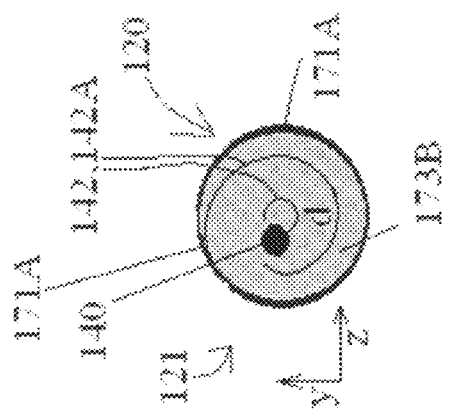
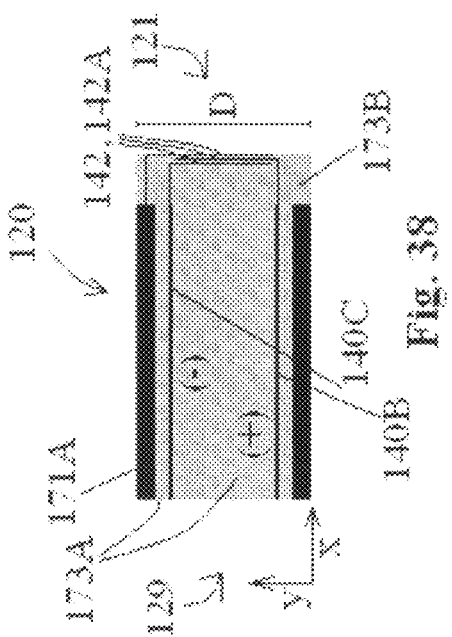
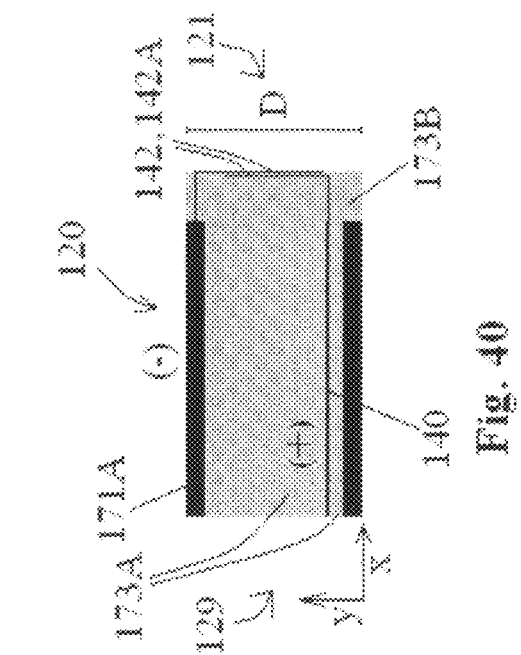

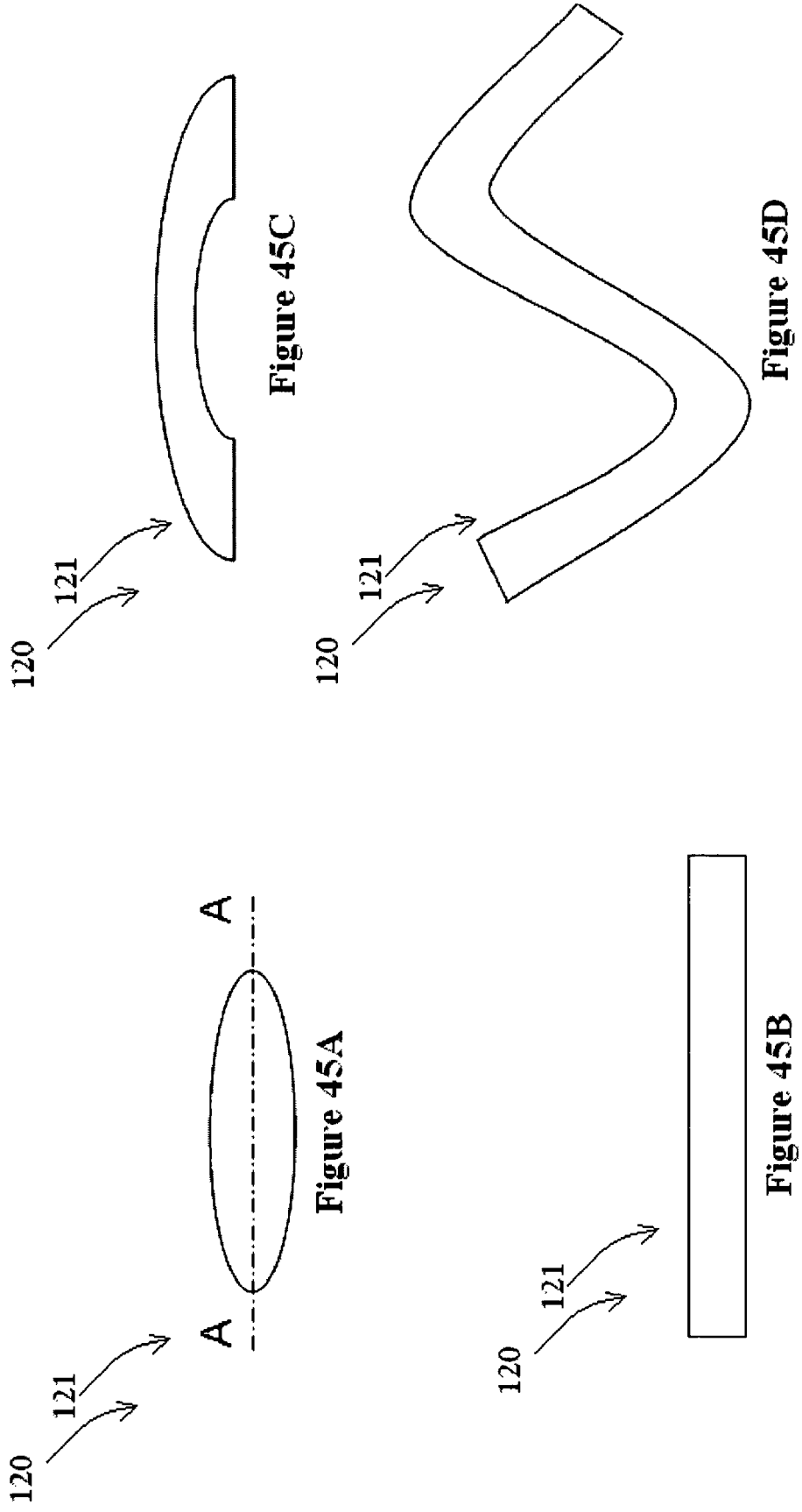

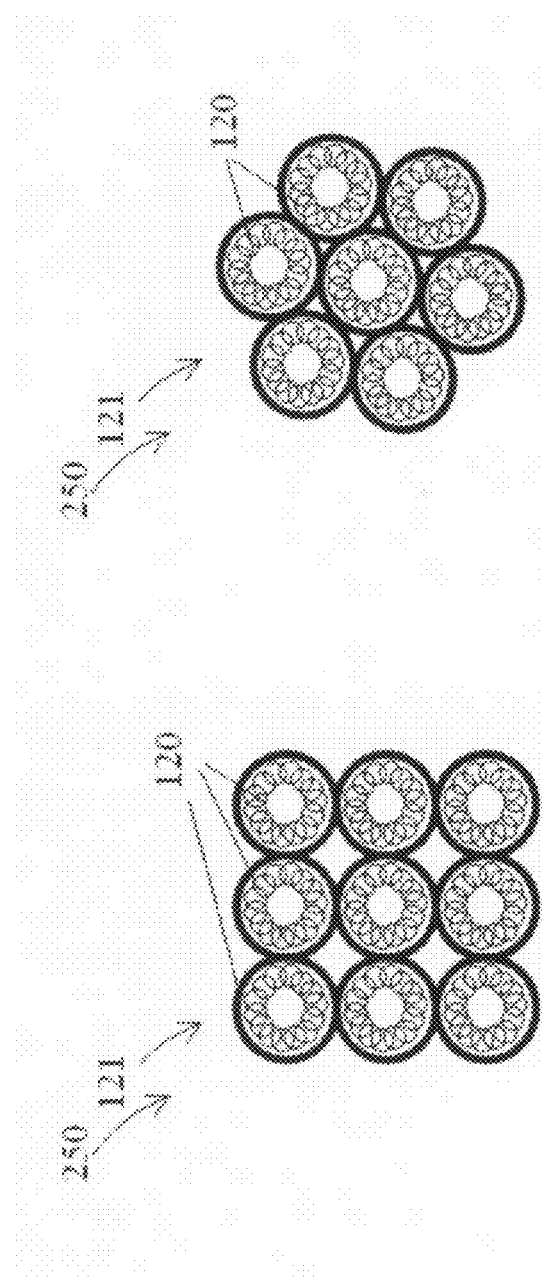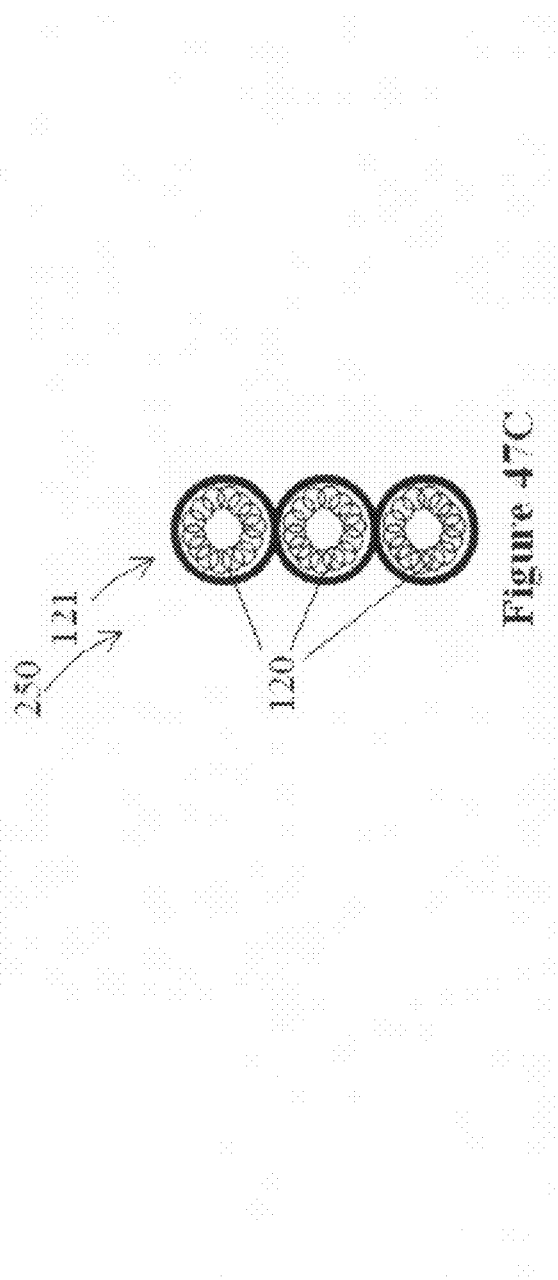

PROBES, SYSTEMS, AND METHODS FOR EXAMINING TISSUE ACCORDING TO THE DIELECTRIC PROPERTIES THEREOF

CROSS REFERENCE TO RELATED APPLICATION

This Application is being co-filed with a sister U.S. Patent Application, entitled "Ergonomic Probes" Ser. No. 11/797,166.

This Application is also a continuation-in-part of U.S. patent application Ser. No. 11/705,143 filed on Feb. 12, 2007, which is a continuation-in-part of U.S. patent application Ser. No. 10/965,752 filed on Oct. 18, 2004, now U.S. Pat. No. 7,184,824 issued on Feb. 27, 2007 and a continuation-in-part of U.S. patent application Ser. No. 10/035,428 filed on Jan. 4, 2002, now U.S. Pat. No. 6,813,515 issued on Nov. 2, 2004.

Additionally, this Application is a continuation-in-part of PCT Patent Application No. PCT/IL2006/000392 filed on Mar. 29, 2006, which claims the benefit of U.S. Provisional Patent Application No. 60/665,842 filed on Mar. 29, 2005, now expired.

Additionally, this Application is a continuation-in-part of pending U.S. patent application Ser. No. 10/567,581 filed on Feb. 8, 2006, which is a National Phase of PCT Patent Application No. PCT/IL2006/000015 filed on Jan. 4, 2006, which claims the benefit of U.S. Provisional Patent Application No. 60/665,842 filed on Mar. 29, 2005, now expired, and U.S. Provisional Patent Application No. 60/641,081 filed on Jan. 4, 2005, now expired.

Additionally, this Application is a continuation-in-part of pending U.S. patent application Ser. No. 10/558,831 filed on Nov. 29, 2005, which is a National Phase of PCT Patent Application No. PCT/IL2005/000330 filed on Mar. 23, 2005, which claims the benefit of U.S. Provisional Patent Application No. 60/555,901 filed on Mar. 23, 2004, now expired.

Additionally, this Application is a continuation-in-part of PCT Patent Application No. PCT/IL2006/000908 filed on Aug. 6, 2006, which is a continuation-in-part of pending U.S. patent application Ser. No. 11/350,102 filed on Feb. 9, 2006, and a continuation-in-part of pending U.S. patent application Ser. No. 11/196,732 filed on Aug. 4, 2005.

Additionally, this Application is a continuation-in-part of U.S. patent application Ser. No. 11/487,431 filed on Jul. 17, 2006, which is a continuation in part of U.S. patent application Ser. No. 10/891,750 filed on Jul. 15, 2004, now U.S. Pat. No. 7,082,325 issued on Jul. 25, 2006.

Additionally, this Application is a continuation-in-part of pending U.S. patent application Ser. No. 10/298,196 filed on Nov. 18, 2002.

Additionally, this Application is a continuation-in-part of pending PCT Patent Application No. PCT/IL2007/000071 on filed on Jan. 18, 2007, which claims the benefit of U.S. Provisional Patent Application No. 60/759,555 filed on Jan. 18, 2006.

The disclosures of all of these are incorporated herein by reference.

FIELD AND BACKGROUND OF THE INVENTION

The present invention relates to probes, systems, and methods for examining and characterizing tissue by its dielectric properties. The invention is particularly useful in differentiating cancerous tissue from normal, healthy tissue.

Breast cancer is the second leading cause of cancer deaths in women today. (after lung cancer) and is the second most common form of cancer among women (after skin cancer). According to the World Health Organization, more than 1.2 million people will be diagnosed with breast cancer this year worldwide. The American Cancer Society estimates that in 2001, approximately 192,200 new cases of invasive breast cancer (Stages I-IV) will be diagnosed among women in the United States; and another 46,400 women will be diagnosed with ductal carcinoma in situ (DCIS), a non-invasive breast cancer. Though much less common, breast cancer also occurs in men, it being estimated that 1,500 cases will be diagnosed in men in 2001. It is further estimated that 40,600 deaths will occur in 2001 from breast cancer (40,200 among women, 400 among men) in the United States. The incidence rate of breast cancer (number of new breast cancers per 100,000 women) increased by approximately 4% during the 1980s but leveled off, to 100.6 cases per 100,000 women, in the 1990s. The death rates from breast cancer also declined significantly between 1992 and 1996, with the largest decreases being among younger women. Medical experts attribute the decline in breast cancer deaths to earlier detection and more effective treatments.

Mammography is currently the best available screening modality for early detection of breast cancer. If the mammography finds a subspecies legion, the individual is directed to undergo a biopsy or other advanced screening methods, like ultrasound or MRI CT etc. Only 20% of the women that undergo a biopsy proceed to a surgical treatment. The traditional method for histological confirmation involves open surgery biopsy. An alternative is image guided biopsy, which is less invasive and more costly. The total number of breast biopsies in the U.S. is about 1.2 M per year. The open biopsy itself is a surgical procedure in which the breast is open and the tumor or lump is taken out, preferably fully.

The traditional method of biopsy, however, is not always successful and fails to successfully remove the appropriate lesion in about 0.5-17% of the cases. Some of the reasons given for unsuccessful biopsies include: 1) poor radiological placement of the localization wire; 2) preoperative and intraoperative dislodgment of the wire; 3) surgical inaccuracy and inadequacy in excising the appropriate tissue; 4) failure to obtain a specimen radiograph; and 5) failure by the pathologist to locate the focus of the disease when searching through a larger tissue sample provided by the surgeon.

All of the above reasons stem from a fundamental problem that during the surgery, the surgeon does not have a real time indication or delineation of the tumor. Because of the difficulty in precisely delineating the cancerous tissue, the surgeon may cut out more than was really necessary to better assure that the entire tumor was removed.

Today, women with stage I and stage II breast cancer are candidates for treatment with modified radical mastectomy and with immediate reconstruction. Breast-conserving therapy (BCT) is also available. Breast conservation therapy consists of surgical removal of a breast nodule and of the auxiliary fat pad containing the auxiliary lymph nodes (about a quarter of the breast). This is followed by radiation therapy to the breast and auxiliary areas in some cases. In this type of operation, precise margin assessment or delineation of the cancerous tissue during the operation is crucial to the success of the procedure since the goal is to remove the tumor completely while minimizing damage to the breast.

This trade-off between complete removal of the tumor, and conservation of the breast, is usually difficult to optimize because the surgeon generally does not know the actual margins of the tumor. If the surgeon were able to clearly delineate the tumor margins during the operation by an on-line margin detector, this trade-off could be better optimized.

The ability of recognizing cancer cells, and especially breast cancer cells, using bioimpedance is well established in the biomedical literature[5,6,7,8]. The usual method for measuring bioimpedance is by introducing a sample into a special chamber and applying an AC current through it while recording the voltage across the sample at each frequency[9,10]. More modern methods rely on multiple electrode matrices which are connected with the human body and measure physiological and pathological changes. Some of the methods aim to localize tumor cells inside the human body and to form an image[11,12]. Although this method is approved by the FDA, it lacks the necessary accuracy for a screening device mainly because of the inherent limitations of long wavelengths and noise from the contact electrodes.

Another technique, based on magnetic[13] bioimpedance, measures the bioimpedance by magnetic induction. This technique consists of a single coil acting as both an electromagnetic source and a receiver operating typically in the frequency range 1-10 MHz. When the coil is placed in a fixed-geometric relationship to a conducting body, the alternating electric field in the coil generates electrical eddy current. A change in the bioimpedance induces changes in the eddy current, and as a result, a change in the magnetic field of those eddy currents. The coil acts as a receiver to detect such changes. Experiments with this technique achieved sensitivity of 95%, and specificity of 69%, distinguishing between 1% metastasis tumor and 20% metastasis tumor. Distinguishing between tumor and normal tissue is even better.

Although the exact mechanism responsible for tissue impedance at certain frequencies is not completely understood, the general mechanism[14,15] is well explained by semi-empirical models that are supported by experiments[16,17,18].

Variations in electrical impedance of the human tissue are described in the patent literature to provide indications of tumors, lesions and other abnormalities. For example, U.S. Pat. Nos. 4,291,708; 4,458,694; 4.537,203; 4,617,939 and 4,539,640 exemplify prior art systems for tissue characterization by using multi-element probes which are pressed against the skin of the patient and measure impedance of the tissue to generate a two-dimensional impedance map. Other prior techniques of this type are described in WO 01/43630; U.S. Pat. Nos. 4,291,708 and 5,143,079. However, the above devices use a set of electrodes that must be electrically contacted with the tissue or body, and therefore the contact is usually a source of noise and also limits maneuverability of the probe over the organ.

Other prior patents, for example U.S. Pat. Nos. 5,807,257; 5,704,355 and 6,061,589 use millimeter and microwave devices to measure bioimpedance and to detect abnormal tissue. These methods direct a free propagating radiation, or a guided radiation via waveguide, onto the organ. The radiation is focused on a relatively small volume inside the organ, and the reflected radiation is then measured. However, these methods lack accuracy and spatial resolution since they are limited by the diffraction limit.

Another prior art technique is based on measurement of the resonance frequency of a resonator as influenced by the tissue impedance. This technique also uses radiation from an antenna, usually a small dipole antenna attached to a coaxial line. Although non-contact, the device actually measures average values inside the organ, and its ability to detect small tumor is doubtful. Similar prior art is described in Xu, Y., et al. "Theoretical and Experimental Study of Measurement of Microwave Permitivity using Open Ended Elliptical Coaxial Probes". IEEE Trans AP-40(1), January 1992, pp 143-150.3. U.S. Pat. No. 6,109,270 (2000 NASA) describes a measurement concept with a multi-modality instrument for tissue identification in real-time neuro-surgical applications.

Other known prior art includes an open-ended coaxial[2,3,4] probe having a center conducting wire surrounding by an insulator and enclosed in an external shield.

Other existing medical instruments provide general diagnoses for the detection of interfaces between different types of tissues, such as cancerous tissue and healthy tissue, etc. However, such detections have been limited clinically to pre-operative scans, or demand large scanning multi-million-dollar machines, like the MRI, CT, and Mammography. Furthermore, real-time attempts to use these detecting methods are very sensitive to movement of the body, and cannot really be used to position the cutting knife or the biopsy needle. Existing devices provide diagnostic data of limited use since the tissue, sampled or removed, depends entirely upon the accuracy with which the localization provided by the preoperative CT, MRI, or US scan is translated to the intracranial biopsy site. Any movement of the organ or the localization device results in an error in biopsy localization. Also, no information about the tissue being cut by the needle or knife is provided.

Detecting breast cancer tissues by measuring biompedance is thus well established, and the ability of this technique for delineating cancerous cells inside the body has been proved. However, there is currently no reliable real-time bioimpedance measuring device of sufficiently high accuracy for local tissue characterization and of a spatial resolution comparable to that provided by mammography.

SUMMARY OF THE INVENTION

The present invention relates to probes, systems, and methods for tissue characterization by its dielectric properties, wherein a physical feature of the probe is designed to define and delimit a tissue volume, at a tissue edge, where characterization takes place. Preferably, tissue characterization occurs substantially in real time.

The probe for tissue-edge characterization is configured for:
  forming contact with a surface of a tissue;
  applying electric signals, associated with a wavelength $\lambda$, to the tissue;
  generating localized electrical and magnetic fringe fields, in the tissue, substantially in a near field, where $x \ll \lambda$;
  producing primary reflected electric signals from the tissue, substantially only from near field; and
  sensing the primary reflected electric signals, from the near field of the tissue.

A novel feature of the probe is its including a physical feature, designed to define and delimit the near field of the tissue, at a tissue edge, where characterization takes place.

Thus, the probe for tissue-edge characterization comprises:
  an inner conductor, having:
    longitudinal axis L along an x-axis of an x;y;z coordinate system; and
    proximal and distal ends, with respect to a tissue, along the x-axis, forming the two endpoints of the longitudinal axis L;
  a first sharp edge 141, inherently associated with the proximal endpoint; and
  the at least one feature, substantially at the proximal end, for forming at least one additional sharp edge, operative to enhance the localized electrical fringe fields in the tissue, within a well defined volume, at the near field, the tissue volume being defined by physical parameters of the feature.

For example, the physical feature may be a wire spiral, having an overall diameter D and a wire diameter d, or wire spacing d. The feature is designed to define and delimit the near field to a tissue volumetric disk, of about a diameter D and a depth d', which is of a same order of magnitude as d. Preferably, the relationship between the overall diameter D and the feature size d is about:

$$1/100 D < d < 1/2 D,$$

where D may be between 2 mm and 10 cm. For example:

For D of about 10 cm, d may be between about 1 mm and about 5 cm.

For D of about 2 mm, d may be between about 20 μm and about 1 mm.

It will thus be appreciated that the depth dimension of the tissue volumetric disk, d', is defined by the feature dimensions to about an order of magnitude.

The at least one feature, having the at least one additional sharp edge is operative to enhance the localized electrical fringe fields, in the tissue volumetric disk, sufficiently, so as to make the sum of reflected electric signals from the tissue outside the tissue volumetric disk less than 1/10 of the primary reflected electric signals, thus making the reflected electric signals from the tissue outside the tissue volumetric disk negligible, when compared with the primary reflected electric signals from the tissue inside the tissue volumetric disk.

In this manner, tissue characterization is at a very localized, well-defined near field, namely, the tissue volumetric disk, with negligible contributions from a far field.

The electrical fringe field is an electrical field that exists at an edge of a charged conductor. Electrical fringe field, as used herein, is time-dependent, as it is produced responsive to time-dependent electric signals.

The electrical fringe field penetration is substantially to the depth d, which is substantially determined by the feature size of the conductor. The profile of the electrical fringe field in the tissue region to the depth d depends on the dielectrical properties of the tissue, which in turn depend on the tissue type—different tissue types will produce different primary reflected electric signals, thus enabling the tissue characterization.

Moreover, the primary reflected electric signals carries with it information about the impedance and dielectric properties of the examined tissue. In consequence, the time-domain-profile of the primary reflected electric signals provides information useful for tissue characterization.

The electrical characteristics of the primary reflected electrical signal are compared with those of the applied (incident) electrical signal by sampling both electrical signals at a plurality of spaced time intervals. Preferably, the sampling rate depends on the highest frequency content of the signal, for example, a sampling rate of every 20 nsec may be applied for a 10 Mhz signal, and a sampling rate of 0.02 nsec may be applied for a 10 Ghz signal. The voltage magnitudes of the two electrical signals at the spaced time intervals are then compared. The reflection coefficient can be also obtained in the frequency domain, both amplitude and phase; and the frequency dependent complex impedance of the tissue is then calculated using the theoretical relation between impedance and reflection.

A first mode of characterization of the examined tissue may be effected by comparing impedance and dielectric properties of the examined tissue with previously stored impedance and dielectric properties of known normal and cancerous tissues. A second mode of characterization may be effected by comparing the Cole-Cole parameters of the examined tissue with those previously stored of known normal and cancerous tissues. A third mode of characterization may be effected by comparing similarities between parametric representations of the signals reflected by the examined tissue with those of previously stored of known normal and cancerous tissues.

In accordance with embodiments of the present invention, the generation of electrical fringe fields in the tissue, substantially to the depth d, as substantially determined by the feature size, with negligible radiation penetrating into and reflected from the tissue beyond the depth d, eliminates almost completely the propagating wave.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the present invention, the description taken with the drawings making apparent to those skilled in the art how the several forms of the present invention may be embodied in practice.

In the drawings:

FIG. 1 schematically illustrates an overall system with a probe for tissue-edge characterization, in accordance with an embodiment of the present invention;

FIG. 2 schematically illustrates a hand-held system with a probe for tissue-edge characterization, in accordance with another embodiment of the present invention;

FIGS. 3A-3E schematically illustrate various constructions of the probe for tissue-edge characterization, in accordance with embodiments of the present invention;

FIGS. 9A-9E schematically illustrate various inner constructions of probes for tissue-edge characterization, in accordance with embodiments of the present invention;

FIGS. 10A-10C schematically illustrate an inner conductor and at least one feature, substantially at the proximal end of the inner conductor, for forming at least one additional sharp edge, in accordance with any one of the embodiments of FIGS. 9A-E;

FIGS. 11A-11C schematically illustrate an inner conductor and features, substantially at the proximal end of the inner conductor, for forming additional sharp edges, in accordance with an embodiment of the present invention;

FIGS. 12A-12C schematically illustrate an inner conductor and features, substantially at the proximal end of the inner conductor, for forming additional sharp edges, in accordance with still another embodiment of the present invention;

FIGS. 13A-13C schematically illustrate an inner conductor and features, substantially at the proximal end of the inner conductor, for forming additional sharp edges, in accordance with yet another embodiment of the present invention;

FIGS. 14A-14C schematically illustrate an inner conductor and features, substantially at the proximal end of the inner conductor, for forming additional sharp edges, in accordance with still another embodiment of the present invention;

FIGS. 15A-15C schematically illustrate an inner conductor and features, substantially at the proximal end of the inner conductor, for forming additional sharp edges, in accordance with yet another embodiment of the present invention;

FIGS. 16A-16C schematically illustrate an inner conductor and features, substantially at the proximal end of the inner conductor, for forming additional sharp edges, in accordance with still another embodiment of the present invention;

FIGS. 17A-17C schematically illustrate an inner conductor and at least one feature, substantially at the proximal end of the inner conductor, for forming at least one additional sharp edge, in accordance with yet another embodiment of the present invention;

FIGS. 18A-18C schematically illustrate an inner conductor and features, substantially at the proximal end of the inner conductor, for forming additional sharp edges, in accordance with still another embodiment of the present invention;

FIGS. 19A-19C schematically illustrate an inner conductor and at least one feature, substantially at the proximal end of the inner conductor, for forming at least one additional sharp edge, in accordance with yet another embodiment of the present invention;

FIGS. 20A-20C schematically illustrate an inner conductor and features, substantially at the proximal end of the inner conductor, for forming additional sharp edges, in accordance with still another embodiment of the present invention;

FIGS. 21A-21C schematically illustrate an inner conductor and features, substantially at the proximal end of the inner conductor, for forming additional sharp edges, in accordance with yet another embodiment of the present invention;

FIGS. 22A-22C schematically illustrate an inner conductor and features, substantially at the proximal end of the inner conductor, for forming additional sharp edges, in accordance with still another embodiment of the present invention;

FIGS. 23A-23C schematically illustrate an inner conductor and features, substantially at the proximal end of the inner conductor, for forming additional sharp edges, in accordance with yet another embodiment of the present invention;

FIGS. 24A-24C schematically illustrate an inner conductor and features, substantially at the proximal end of the inner conductor, for forming additional sharp edges, in accordance with still another embodiment of the present invention;

FIGS. 25A-25C schematically illustrate an inner conductor and features, substantially at the proximal end of the inner conductor, for forming additional sharp edges, in accordance with yet another embodiment of the present invention;

FIGS. 25D-25E schematically illustrate the probe associated with FIGS. 25A-25C, with inductive and resistive coupling, respectively, in accordance with embodiments of the present invention;

FIGS. 26A-26C schematically illustrate an inner conductor and features, substantially at the proximal end of the inner conductor, for forming additional sharp edges, in accordance with still another embodiment of the present invention;

FIGS. 27A-27C schematically illustrate an inner conductor and features, substantially at the proximal end of the inner conductor, for forming additional sharp edges, in accordance with yet another embodiment of the present invention;

FIGS. 28A-28C schematically illustrate an inner conductor and features, substantially at the proximal end of the inner conductor, for forming additional sharp edges, in accordance with still another embodiment of the present invention;

FIGS. 29A-29C schematically illustrate an inner conductor and features, substantially at the proximal end of the inner conductor, for forming additional sharp edges, in accordance with yet another embodiment of the present invention;

FIGS. 30A-30C schematically illustrate an inner conductor and features, substantially at the proximal end of the inner conductor, for forming additional sharp edges, in accordance with still another embodiment of the present invention;

FIGS. 31A-31C schematically illustrate an inner conductor and features, substantially at the proximal end of the inner conductor, for forming additional sharp edges, in accordance with yet another embodiment of the present invention;

FIGS. 32A-32C schematically illustrate an inner conductor and features, substantially at the proximal end of the inner conductor, for forming additional sharp edges, in accordance with still another embodiment of the present invention;

FIGS. 33A-33B schematically illustrate an inner construction of a probe for tissue-edge characterization, in accordance with an embodiment of the present invention;

FIGS. 33C-33D schematically illustrate an inner construction of a probe for tissue-edge characterization, in accordance with another embodiment of the present invention;

FIGS. 34A-34B schematically illustrate an inner construction of a probe for tissue-edge characterization, in accordance with still another embodiment of the present invention;

FIG. 35 schematically illustrates an inner construction of a probe for tissue-edge characterization, with two inner conductors, in accordance with embodiments of the present invention;

FIG. 36 schematically illustrates a proximal view of a probe for tissue-edge characterization, in accordance with an embodiment, based on FIG. 35;

FIGS. 37A and 37B schematically illustrate a proximal view of another probe for tissue-edge characterization, in accordance with embodiments, based on FIG. 35;

FIG. 38 schematically illustrates another inner construction of a probe for tissue-edge characterization, with two inner conductors, in accordance with embodiments of the present invention;

FIG. 39 schematically illustrates a proximal view of a probe for tissue-edge characterization, in accordance with an embodiment, based on FIG. 38;

FIG. 40 schematically illustrates another inner construction of a probe for tissue-edge characterization, in accordance with embodiments of the present invention;

FIG. 41 schematically illustrates a proximal view of a probe for tissue-edge characterization, in accordance with an embodiment, based on FIG. 41;

FIGS. 45A-45D schematically illustrate proximal ends of probes of various shapes, in accordance with embodiments of the present invention;

FIGS. 47A-47F schematically illustrate arrays of probes, each operative as a single testing device for tissue-edge characterization, in accordance with embodiments of the present invention.

DESCRIPTION OF THE PREFERRED EMBODIMENTS

Figure 4:
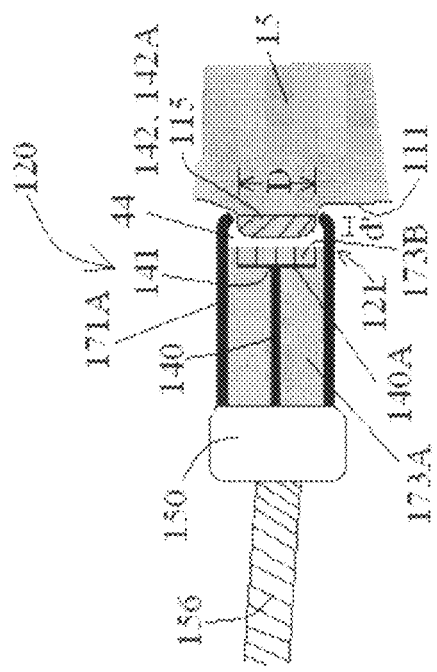
FIG. 4 schematically illustrates a probe constructed with a cavity, in accordance with an embodiment of the present invention.

The present invention relates to probes, systems, and methods for tissue characterization by its dielectric properties, wherein a physical feature of the probe is designed to define and delimit a tissue volume, at the tissue edge, where characterization takes place. Preferably, tissue characterization occurs substantially in real time.

Before explaining at least one embodiment of the present invention in detail, it is to be understood that the present invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 schematically illustrates an overall system 110 with a probe 120 for tissue-edge characterization, in accordance with an embodiment of the present invention.

The probe 120 for tissue-edge characterization is configured for:

forming contact with a surface 111 of a tissue 15;

applying electric signals, associated with a wavelength $\lambda$, to the tissue 15;

generating localized electrical and magnetic fringe fields 112, in the tissue 15, substantially in a near field 117, where $x \ll \lambda$;

producing primary reflected electric signals from the tissue 15, substantially only from near field 117; and sensing the primary reflected electric signals, from the near field 117 of the tissue 15.

A novel feature of the probe 120 is its including a physical feature 142, designed to define and delimit the near field 117 of the tissue 15, where characterization takes place.

Thus, the probe 120 for tissue-edge characterization comprises:

an inner conductor 140, having:

a longitudinal axis L along an x-axis of an x;y;z coordinate system; and proximal and distal ends 121 and 129, with respect to a tissue 15, along the x-axis, forming the two endpoints of the longitudinal axis L;

a first sharp edge 141, inherently associated with the proximal endpoint 121; and the at least one feature 142, substantially at the proximal end 121, for forming at least one additional sharp edge 142A, operative to enhance the localized electrical fringe fields in the tissue, within a well defined volume, at the near field, the tissue volume being defined by the physical parameters of the feature 142.

For example, the physical feature 142 may be a wire spiral, having an overall diameter D and a wire diameter d, or wire spacing d. The feature 142 is designed to define and delimit the near field 117 to a tissue volumetric disk, of about a diameter D and a depth d', which is of about the same order of magnitude as d. Preferably, the relationship between the overall diameter D and the feature size d is about, $\frac{1}{100} D < d < \frac{1}{2} D$, where D may be between 2 mm and 10 cm. For example:

For D of about 10 cm, d may be between about 1 mm and about 5 cm.

For D of about 2 mm, d may be between about 20 μm and about 1 mm.

It will thus be appreciated that the depth dimension of the tissue volumetric disk, d', is defined by the feature dimensions to about an order of magnitude.

The at least one feature 142, having the at least one additional sharp edge 142A is operative to enhance the localized electrical fringe fields 112, in the tissue volumetric disk 115, sufficiently, so as to make the sum of reflected electric signals from the tissue 15 outside the tissue volumetric disk 115 less than $\frac{1}{10}$ of the primary reflected electric signals, thus making the reflected electric signals from the tissue 15 outside the tissue volumetric disk 115 negligible, when compared with the primary reflected electric signals from the tissue 15 inside the tissue volumetric disk 115.

In this manner, tissue characterization is at a very localized, well-defined near zone 117, namely, the tissue volumetric disk 115, with negligible contributions from a far zone 119.

As seen in FIG. 1, the probe 120 may be associated with an external control and instrumentation system 130 for signal generation and analysis, which together form the overall system 110 for tissue-edge characterization.

Accordingly, the probe 120 may be associated with a transmission line 156, directly connected to the probe 120, or coupled to the probe 120 via a coupler 150, preferably, at the distal end 129. The transmission line 156 leads to the external control and instrumentation system 130 and is operative to transmit a signal to an inner conductor 140, for applying electric signals to the tissue 15, and to transmit back a response signal, which corresponds to the primary reflected electric signals.

The external control and instrumentation system 130 may include a signal generator 132, a signal analyzer 134, and a controller 136, with various memories. It will be appreciated that these may be integrated into a single unit. A user interface may be provided, for example, in the form of a keyboard 135, for example, to input data such as patient details, date and time of a particular test, and other relevant data.

Additionally, the external control and instrumentation system 130 may include read and write drives 131, for example, diskettes, CDs, and (or) DVDs, for input and output of predetermined operating parameters and settings, and (or) in order to store test results. A USB port 133 for example, for a disk-on-key, and other ports may be provided. A display screen 138 may display the response and may further be a touch screen, operative as a user interface, additional to or in place of the keyboard 135.

The external control and instrumentation system 130 may further include output means, for example, a printer or a facsimile.

Additionally or alternatively, the external control and instrumentation system 130 may be configured for internet and (or) wireless internet connection.

It will be appreciated that the systems described in FIGS. 6-8 hereinbelow may similarly be employed.

Referring further to the drawings, FIG. 2 schematically illustrates a hand-held system 110 with the probe 120 for tissue-edge characterization, in accordance with another embodiment of the present invention.

Accordingly, in FIG. 2, the probe 120 is shown as part of a stand-alone, hand-held system 110 configured for internal signal generation and analysis. As such, a control and instrumentation system 130A is integrated with the probe 120, for example, within a handle 240, and includes the signal generator 132, the signal analyzer 134, the controller 136 and the various memories. Preferably, the stand-alone, hand-held system 110 further includes the display screen 138, keys 135 as well as additional control keys 135A, a USB port 133, internet connection, wireless internet connection, and other features, as known.

It will be appreciated that the control features described in FIGS. 6-8 hereinbelow may be employed with the stand-alone, hand-held system 110 of FIG. 2.

Referring further to the drawings, FIGS. 3A-3E schematically illustrate various constructions of the probe for tissue-edge characterization, in accordance with embodiments of the present invention.

As seen in FIG. 3A, the probe 120 includes an inner conductor 140 surrounded by a dielectric material 173A, an inner conductor 140 defining the first sharp edge 141, which in accordance with the present example, is not configured for making contact with the tissue 15. The at least one feature 142 is substantially at the proximal end 121, forming the additional sharp edges 142A, associated with the sizes D and d, defined in the y-z plane, substantially parallel with the surface 111 of the tissue 15. The additional sharp edges 142A are configured for making contact with the tissue 15. The transmission line 156 is coupled to an inner conductor 140, via the coupler 150. In accordance with the present embodiment, the feature 142 is exposed to air.

As seen in FIG. 3B, the feature 142 is embedded in a thin insulating layer of dielectric material 173B, of about 1-200 μm, for example, of polyimide (Kapton), Polytetrafluoroethylene-PTFE (tefon), PolyEtherImide (Ultem), or another dielectric material, as known.

As seen in FIG. 3C, a conductive outer sleeve 171A may be employed, for surrounding an inner conductor 140 and the dielectric material 173A within. The conductive outer sleeve 171A serves as a return path for signals generated at the proximal end 121 of the inner conductor 140.

In accordance with the present example, the feature 142 is inductively coupled to the conductive outer sleeve 171A.

As seen in FIG. 3D, the conductive outer sleeve 171A is employed, and the feature 142 is resistively coupled to the conductive outer sleeve 171A.

As seen in FIG. 3E, a thin layer of a dielectric material 173C is deposited on the proximal end of the feature 142. Accordingly, the thin layer of a dielectric material 173C makes contact with the tissue surface 111, rather then the conductive elements of the feature 142.

Referring further to the drawings, FIG. 4 schematically illustrates a probe constructed with a cavity, in accordance with an embodiment of the present invention.

As seen in FIG. 4, the conductive outer sleeve 171A extends proximally, beyond the feature 142, to form a cavity 44. The tissue edge is characterized within the cavity 44, as the cavity 44 is adapted for containing the tissue volumetric disk 115 therein. In some cases, the probe outer conductor 171A may taper in slightly, at its proximal end 121.

Figure 5:
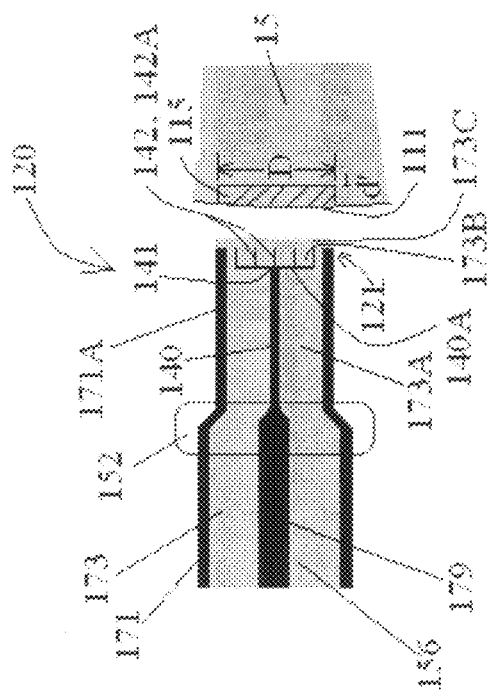
FIG. 5 schematically illustrates a probe with a coaxial cable operative as a transmission line, in accordance with an embodiment of the present invention.

Referring further to the drawings, FIG. 5 schematically illustrates a probe with a coaxial cable operative as a transmission line, in accordance with an embodiment of the present invention. As seen in FIG. 5, the transmission line 156 may be constructed as a coaxial cable having an inner conductor 179, an outer sleeve 171, and a dielectric material 173 therebetween. The coaxial cable 156 is coupled to the probe 120 via a coupler 152.

Figure 6:
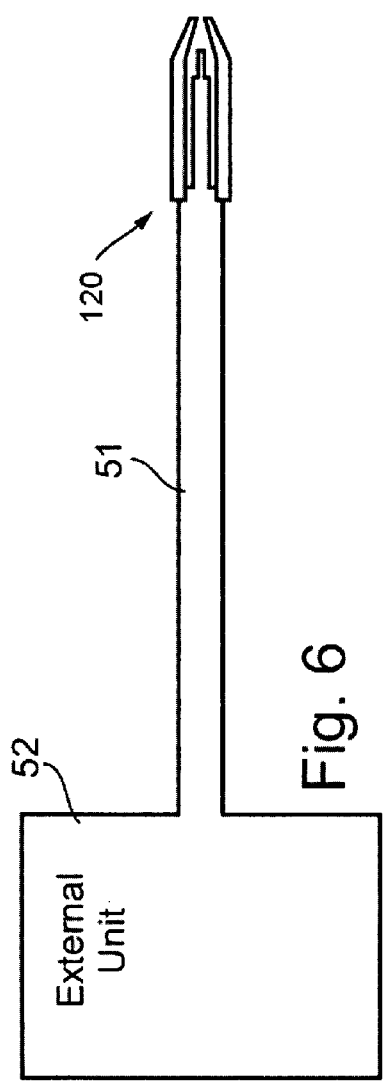
FIG. 6 schematically illustrates a probe constructed in accordance with embodiments of the present invention, connected to an external unit by a flexible coaxial line.

Referring further to the drawings, FIG. 6 schematically illustrates a probe constructed in accordance with embodiments of the present invention, connected to an external unit 52 by a flexible transmission line, for example, a coaxial line 51. Accordingly, a probe 120, such as that illustrated in FIGS. 1-3E, coupled to one end of a flexible coaxial line 51; the opposite end of coaxial line 51 is connected to an external unit 52 for supplying the electrical signals to the probe. The external unit 52 is more particularly illustrated in FIG. 7, as including a computer 53, a signals source 54 and a digitizing unit 55. The electrical signals may be in the form of, for example, a sinusoidal signal, a square pulse, a triangular pulse, a chirped pulse, a modulated pulse, a tailored pulse, or any other pulse known in the art.

The at least one feature 142, with the additional sharp edges 142A produce a modified coaxial mode, leading to a much stronger electrical fringing field in the tissue, in the volumetric disk 115. In this way, only the small portion of the biological tissue placed within the volume where the electric fringing field is present and is responsible for most of the reflection of the applied electrical signals back into the transmission line 51. The output impedance of the probe thus depends to a great extent on the impedance of the biological tissue within the volume where the electric fringing field is present—the volumetric disk 115. As a result, the reflected signal detected by the probe is dependent substantially on the impedance and dielectric properties of the tissue itself. This allows a well defined volume of sampled tissue impedance to be calculated without affecting, or being affected by, the surrounding tissues.

Figure 7:
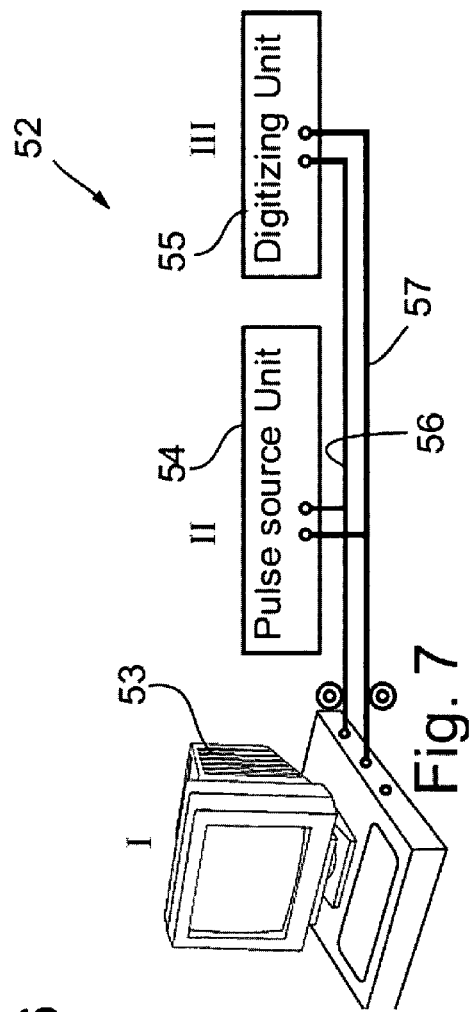
FIG. 7 schematically illustrates components of the external unit in the system of FIG. 6.

Referring further to the drawings, FIG. 7 schematically illustrates components of the external unit 52 in the system of FIG. 6.

As shown in FIG. 7, two sets of wires 56, 57 connect the computer 53 to the signals source unit 54 and the digitizing unit 55. One set of wires 56 are the timing control wires used to transmit trigger signals to the signal source unit 54 and the digitizing unit 55; whereas the other set of wires 57 are the data transfer wires used to transfer data from and to the computer 53.

The computer 53 controls the signal durations and repetition rates, as well as the signal voltage and form.

Figure 8:
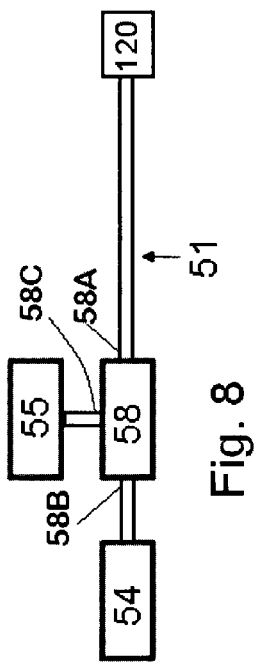
FIG. 8 illustrates a connector between the external unit components and the coaxial line to the probe, in accordance with the present invention.

Referring further to the drawings, FIG. 8 illustrates a connector between the external unit components and a coaxial line to the probe, in accordance with embodiments of the present invention;

FIG. 8 illustrates an electrical signal coupler 58 connecting the signal source unit 54, the digitizing unit 55, and the probe 120.

As shown in FIG. 8, these connections are made by an electrical signal coupler 58 having one leg 58A connected to the coaxial line 51, a second leg 58B connected to the signal source unit 54, and a third leg 58C connected to the digitizing unit 55.

Digitizing unit 55 samples, at a plurality of spaced time intervals, both the incident electrical signals, namely those applied to the probe 120, and the reflected signals reflected by the examined tissue in the volumetric disk 115.

The two time-domain arrays may also be transformed to the frequency domain, for example, by a conventional FFT program, which is a standard tool for transforming time domain signals to the frequency domain.

The above-described procedure is repeated, e.g., 1,000-10,000 times, for each measurement point. This result is 1,000-10,000 pairs of arrays, all of which are saved and transmitted to the analysis program of the computer 53.

Computer 53 compares the electrical characteristics of the reflected electrical signals with respect to those of the incident (applied) electrical signals to provide an indication of the impedance and dielectric properties of the examined tissue. This is done by sampling both electrical signals at a plurality of spaced time intervals, and comparing the voltage magnitudes of the two electrical signals at the spaced time intervals.

The foregoing comparison is made using one, or a combination of, type of analysis: (1) an impedance or dielectric function calculation, (2) a Cole-Cole parameters calculation, and (3) Parametric representation of the reflection signal After the impedance and/or dielectric function of the examined tissue is calculated, it may also be analyzed according to, for example but not limited to, the following procedures for feature extraction:

The computer calculated the values of extreme point (Peaks) and special features, like the frequency at which the extreme points appear, the amplitude of the peaks, the average value of the function, the integral under the real part of the dielectric function, the average value of the derivative, the maximum derivative, and the roots of the function. All these values are transferred as an array of parametric representation of the reflected signal to the decision-making program routine. For each value the statistical variance is also calculated.

In the Cole-Cole Parameter analysis the Cole-Cole parameters τ and α of the sampled tissue are calculated from the dielectric function as follows:

$$\varepsilon = \varepsilon_\infty + \frac{\Delta\varepsilon}{(1+j\omega\tau_c)^{1-\alpha}}, \Delta\varepsilon = \varepsilon_s - \varepsilon_\infty \qquad (Eq.\ 5)$$

Where: e is the dielectric function of the sample; $\varepsilon_\infty$ is the dielectric function at infinite frequency=constant; $\varepsilon_0$ is the dielectric function under dc field=constant; and j is $(-1)^{1/2}$ For each value, the statistical variance is also calculated. After calculation, the Cole-Cole parameters are transferred to the decision-making program routine.

The decision making routine compares the results from any combination of the three types of analysis and the existing data from the memory bank. In the memory bank, data from known types of tissue is recorded, together with the tissue type name and the statistical variance. The statistical variance is used to define a volume surrounding the curve.

The matching condition is a standard statistical process which compares two sets of data. It uses all data for comparison. For example, if the data matches data from a previously taken memory bank data, the program displays the type of tissue from which the databank sample was taken.

In case there is no match between stored (known) tissue data and the examined tissue data, the most similar stored tissue data is chosen as characterizing the examined tissue. The most similar tissue is chosen according to the distance (in the phase space) between the two measured points; alternatively, a user defined criterion may be applied. The user may decide to find similarities, at certain measurement points, based on one, two, or more specific calculated parameters, ignoring all the others. For example the user may decide to find similarities only according to the frequency at which a peak appears in the real-part of the dielectric function.

The decision making routine also compares the last-point measured to the currently measured point. The result of that process is to indicate merely how similar the two points are to each other, without knowing the type of tissue of the last point. The distance between two data points is considered as usually in statistics, and the decisions are displayed on the screen together with all data parameters.

Referring further to the drawings, FIGS. 9A-9E schematically illustrate various inner constructions of probes for tissue-edge characterization, in accordance with embodiments of the present invention.

As seen in FIGS. 9A-9E, the feature 142 is a step reduction in diameter of the inner conductor 140, leading to addition sharp edges, due to the corners formed by the step. The probe 120 itself may be constructed in various ways, as follows, As seen in FIG. 9A, the inner conductor 140 of the probe 120 is of the diameter D, which generally defines the diameter of the volumetric disk 115 (FIG. 1).

An inner conductor 140 is surrounded by a dielectric material 173A, which in accordance with the present embodiment, is exposed to air.

The feature 142, being the step reduction in diameter, may be embedded in a dielectric material 173B. Alternatively, the feature 142 may be exposed to air.

As seen in FIG. 9B, the probe 120 may further include the conductive outer sleeve 171A.

As seen in FIG. 9C, the inner conductor 120 may be thinner than the diameter D, and the feature 142 may further include a conducting disk 140A, which defines the diameter D, and from which the step change in diameter takes place.

In accordance with the present embodiment, the feature 142 is inductively coupled to the conductive outer sleeve 17 1A.

As seen in FIG. 9D, a layer of dielectric material 173C may be deposited on the feature 142, so that contact with the tissue surface 111 (FIG. 1) is made by the dielectric material 173C.

As seen in FIG. 9E, the conductive outer sleeve 171A may be extended beyond the feature 142, so as to form a cavity 44, where interaction with the tissue volumetric disk 115 takes place. (See also FIG. 4.)

Referring further to the drawings, FIGS. 10A-10C illustrate side, proximal, and perspective views, respectively, of an inner conductor 140, of FIGS. 9A or 9B, in accordance with embodiments of the present invention. Accordingly, an inner conductor 140 has a circular cross section, with the diameter D being substantially equal to 3d. Additionally, an inner conductor 140 includes a proximal-end face 147, which is substantially a flat face, substantially parallel to the y;z plane, and the feature 142 issues from the proximal-end face 147. The at least one feature 142 is a step reduction in the diameter D, by d, forming a step 142B, in the direction of +x. The step 142B creates the additional sharp edge 142A.

As a result, the first sharp edge 141 and the additional sharp edge 142A of the feature 142 form two concentric sharp edges, separated substantially by d, when viewed from the proximal end 121, as seen in FIG. 10B.

The additional sharp edge 142A associated with the size d is operative to enhance the localized electrical fringe fields 112, in the tissue volumetric disk 115, of a general diameter D and of a depth of generally d' which is of about a same order of magnitude as d. The enhancement is sufficiently so as to make the reflected electric signals from the tissue 15 outside the tissue volumetric disk 115 negligible, when compared with the primary reflected electric signals.

It will be appreciated that the other embodiments described in conjunction with FIGS. 9C-9E may similarly apply.

Referring further to the drawings, FIGS. 11A-11C illustrate side, proximal, and perspective views, respectively, of an inner conductor 140, in accordance with another embodiment of the present invention, wherein the at least one feature 142 is at least two step reductions in the diameter D, by d, forming steps 142B, in the direction of +x, and creating the additional sharp edges 142A.

Preferably, as seen in FIG. 11B, when viewed from the proximal end the sharp edges 142A appear as concentric circles, separated substantially by d. Furthermore, the first sharp edge 141 is also separated from its adjacent sharp edge 142A substantially by d. The plurality of sharp edges 142A enhance the localized electrical fringe fields 112 in the tissue volumetric disk 115.

It will be appreciated that the other embodiments described in conjunction with FIGS. 9A-9E may similarly apply here as well.

Referring further to the drawings, FIGS. 12A-12C illustrate side, proximal, and perspective views, respectively, of an inner conductor 140, in accordance with yet another embodiment of the present invention, wherein an inner conductor 140 includes a carved-out portion 149, in the −x direction, at the proximal end 121, and further wherein the at least one feature 142 issues from the carved-out portion 149, so that the at least one additional sharp edge 142A is substantially at the same x position as the first sharp edge 141.

In accordance with the present embodiment, the at least one feature 142 is step reductions in the diameter D, by d, forming steps 142B, alternating in directions between +x and −x.

When viewed from the proximal end (FIG. 12B), the sharp edges 142A formed by the steps 142B appear as concentric circles, separated substantially by d, enhancing the localized electrical fringe fields 112 in the tissue volumetric disk 115. Preferably the first sharp edge 141 is also separated from the nearest sharp edge 142A, by d.

It will be appreciated that many variations of step changes are possible, for example, step increases in the diameter D, by d, in either the +x or the −x direction, and various combinations of the +x and −x directions.

It will be appreciated that the other embodiments described in conjunction with FIGS. 9A-9E may similarly apply here as well.

Referring further to the drawings, FIGS. 13A-13C illustrate side, proximal, and perspective views, respectively, of an inner conductor 140, in accordance with still another embodiment of the present invention. As these Figures illustrate, an inner conductor 140 has a polygonal cross section. The diameter equivalent of the polygon is defined here as the diameter of a circle of an area equal to the area of the polygon.

The at least one feature 142 is the polygon corners, which define the additional sharp edges 142A. In the present example, D≈2d and the polygon is a hexagon, so that when viewed from the proximal end (FIG. 13B), the polygon corners are separated by distances d.

It will be appreciated that the other embodiments described in conjunction with FIGS. 9A-9E may similarly apply here as well. However, in place of a round disk 140A, a polygonal disk 140A may be employed.

Referring further to the drawings, FIGS. 14A-14C illustrate side, proximal, and perspective views, respectively, of an inner conductor 140, in accordance with yet another embodiment of the present invention, illustrating the polygonal conductor 140, as is FIGS. 13A-13C, wherein the at least one feature 142 further includes step changes in the diameter equivalent D, in a manner analogous to that of FIGS. 11A-11C, so as to create a series of sharp edges 142A of concentric polygons, separated by distances d, when viewed from the proximal end 121 (FIG. 14B).

It will be appreciated that the other embodiments described in conjunction with FIGS. 9A-9E may similarly apply here as well. However, in place of a round disk 140A, a polygonal disk 140A may be employed.

Referring further to the drawings, FIGS. 15A-15C illustrate side, proximal, and perspective views, respectively, of an inner conductor 140, in accordance with still another embodiment of the present invention, illustrating the polygonal conductor 140, as is FIGS. 13A-13C, wherein the at least one feature 142 further includes step changes in the diameter equivalent D, alternating in directions between +x and −x, in a manner analogous to that of FIGS. 12A-12C, again creating a series of sharp edges 142A of concentric polygons, when viewed from the proximal end 121 (FIG. 15B).

It will be appreciated that the other embodiments described in conjunction with FIGS. 9A-9E may similarly apply here as well. However, in place of a round disk 140A, a polygonal disk 140A may be employed.

Referring further to the drawings, FIGS. 16A-16C illustrate side, proximal, and perspective views, respectively, of the inner conductor 140, in accordance with yet another embodiment of the present invention, wherein D is substantially equal to 2d, and the inner conductor 140 is carved out at the proximal end, as an inverse cone, to a depth no greater than substantially d, in the −x direction, forming the inverse-cone, carved-out portion 149, wherein the at least one feature 142 is the inverse cone apex, forming the at least one additional sharp edge 142A, and further wherein the first sharp edge 141 and the apex 142A create two concentric sharp edges, separated substantially by d, when viewed from the proximal end 121 (FIG. 16B).

It will be appreciated that the other embodiments described in conjunction with FIGS. 9A-9E may similarly apply here as well.

Referring further to the drawings, FIGS. 17A-17C illustrate side, proximal, and perspective views, respectively, of an inner conductor 140, in accordance with still another embodiment of the present invention. Accordingly, an inner conductor 140 further includes a proximal-end face 147, which is substantially flat, in the y;z plane, and D is substantially equal to 2d. The at least one feature 142 is a needle 142, having a needle diameter δ (FIGS. 17A and 17B), which is preferably no greater than substantially ½ d. Preferably, the needle 142 issues from the center of the proximal-end face 147, its proximal end forming the at least one additional sharp edge 142A, so that the first sharp edge 141 and the needle's sharp edge 142A create two concentric sharp edges, separated substantially by d, when viewed from the proximal end 121 (FIG. 17B).

It will be appreciated that the other embodiments described in conjunction with FIGS. 9A-9E may similarly apply here as well.

Referring further to the drawings, FIGS. 18A-18C illustrate side, proximal, and perspective views, respectively, of the inner conductor 140, in accordance with still another embodiment of the present invention, wherein the inner conductor 140 is formed with carved grooves 142, forming concentric sharp edge 142A, separated substantially by d, when viewed from the proximal end 121 (FIG. 18B).

It will be appreciated that the other embodiments described in conjunction with FIGS. 9A-9E may similarly apply here as well.

Referring further to the drawings, FIGS. 19A-19C schematically illustrates the inner conductor 140, with the feature 142 being a needle issuing from a carved out portion 149.

Accordingly, the inner conductor 140 has a conical proximal end, the cone being carved out in the −x direction, to a depth no greater than substantially D, forming an inverse-cone, carved-out portion 149, wherein the at least one feature 142 is a needle having a needle diameter δ, the needle issuing from the center of the inverse-cone, carved-out portion 149, its proximal end forming the at least one additional sharp edge 142A, wherein the first sharp edge 141 and the needle's sharp edge 142A creates two concentric sharp edges, separated substantially by d, when viewed from the proximal end 121 (FIG. 19B), and having substantially the same x position (FIG. 19A).

It will be appreciated that the other embodiments described in conjunction with FIGS. 9A-9E may similarly apply here as well.

Referring further to the drawings, FIGS. 20A-20C illustrate side, proximal, and perspective views, respectively, of an inner conductor 140, in accordance with another embodiment of the present invention. An inner conductor 140 includes the carved-out portion 149, in the proximal end 121, and the at least one feature 142 is a plurality of the needles of the needle diameters δ, no greater than substantially ½ d, issuing from the carved-out portion 149, and separated substantially by distances d, therebetween. The needles' proximal ends form a plurality of sharp edges 142A, separated substantially by d therebetween, when viewed from the proximal end 121 (FIG. 20B). Additionally, the carved-out portion 149 forms an additional sharp edge 142A, preferably separated from the first sharp edge 141 substantially by the distance d, (FIG. 20B). Preferably, all the sharp edges have substantially the same x position (FIG. 20A).

It will be appreciated that the other embodiments described in conjunction with FIGS. 9A-9E may similarly apply here as well.

Referring further to the drawings, FIGS. 21A-21C illustrate side, proximal, and perspective views, respectively, of an inner conductor 140, in accordance with yet another embodiment of the present invention, wherein the at least one feature 142 is a plurality of the needles of the needle diameters δ, no greater than substantially ½ d, issuing from the proximal-end face 147 of an inner conductor 140, and separated substantially by distances d, therebetween, wherein the needles proximal ends form a plurality of sharp edges 142A, separated substantially by d therebetween, when viewed from the proximal end 121 (FIG. 21B).

It will be appreciated that the other embodiments described in conjunction with FIGS. 9A-9E may similarly apply here as well.

Referring further to the drawings, FIGS. 22A-22C illustrate side, proximal, and perspective views, respectively, of an inner conductor 140, in accordance with still another embodiment of the present invention. Accordingly, the at least one feature 142 is a carving of bars on the proximal-end face 147 of an inner conductor 140. The bars are of a thickness of substantially d and are separated substantially by d. The bars form a plurality of sharp edges 142A, separated substantially by d therebetween, when viewed from the proximal end 121 (FIG. 22B).

It will be appreciated that the other embodiments described in conjunction with FIGS. 9A-9E may similarly apply here as well.

Referring further to the drawings, FIGS. 23A-23C illustrate side, proximal, and perspective views, respectively, of an inner conductor 140, in accordance with yet another th embodiment of the present invention. Accordingly, an inner conductor 140 has a square cross section and the at least one feature 142 is a square checkerboard carving, on the proximal-end face 147 of an inner conductor 140. The checkerboard carving is of squares of sides that are substantially d, so that the squares form a plurality of sharp edges 142A, separated substantially by d therebetween, when viewed from the proximal end 121 (FIG. 23B).

It will be appreciated that the other embodiments described in conjunction with FIGS. 9A-9E may similarly apply here as well, yet where the disk 140A is employed it will have a rectangular cross section.

Referring further to the drawings, FIGS. 24A-24C illustrate side, proximal, and perspective views, respectively, of an inner conductor 140, in accordance with still another embodiment of the present invention, similar to that of FIGS. 23A-23C; however, with an inner conductor 140 having a circular cross section.

It will be appreciated that the other embodiments described in conjunction with FIGS. 9A-9E may similarly apply here as well.

Referring further to the drawings, FIGS. 25A-25C illustrate side, proximal, and perspective views, respectively, of an inner conductor 140, in accordance with yet another embodiment of the present invention. Accordingly, the at least one feature 142 is a square grid construction, formed of squares of sides that are substantially d, of the conductive wire of the wire diameter δ, the squares forming a plurality of sharp edges 142A, separated substantially by d therebetween, when viewed from the proximal end 121 (FIG. 25B).

Referring further to the drawings, FIGS. 25D and 25E schematically illustrate the probe 120 associated with FIGS. 25A-25C, wherein the feature 142 is inductively coupled to the condutctive outer sleeve 171A (FIG. 25D) or resistively coupled to the conductive outer sleeve 171A (FIG. 25E). Preferably, when the feature 142 is resistively coupled, as in FIG. 25E, the thin inner conductor shown in FIG. 25E is preferred to the inner conductor of the diameter of substantially D, shown in FIGS. 25A-25C.

It will be appreciated that the other embodiments described in conjunction with FIGS. 9A-9E may similarly apply here as well.

Referring further to the drawings, FIGS. 26A-26C illustrate side, proximal, and perspective views, respectively, of an inner conductor 140, in accordance with still another embodiment of the present invention, wherein the at least one feature 142 is a wire construction of slots, of the conductive wire of the wire diameter δ, and further wherein the slots are substantially of a width d, when viewed from the proximal end 121 (FIG. 26B).

It will be appreciated that the other embodiments described in conjunction with FIGS. 9A-9E and FIGS. 25D-25E may similarly apply here as well.

Referring further to the drawings, FIGS. 27A-27C illustrate side, proximal, and perspective views, respectively, of an inner conductor 140, in accordance with yet another embodiment of the present invention, wherein the at least one feature 142 is a wire construction, issuing from an inner conductor 140 and bent into shapes that define the size d, when viewed from the proximal end 121 (FIG. 27B), formed of the conductive wire of the wire diameter δ, no greater than substantially ½ d.

It will be appreciated that the other embodiments described in conjunction with FIGS. 9A-9E and FIGS. 25D-25E may similarly apply here as well.

Referring further to the drawings, FIGS. 28A-28C illustrate side, proximal, and perspective views, respectively, of an inner conductor 140, in accordance with a still another embodiment of the present invention, wherein the at least one feature 142 is at least two wire constructions, issuing from an inner conductor 140 and bent into shapes that define the size d, when viewed from the proximal end 121 (FIG. 28B), formed of the conductive wire of the wire diameter δ, no greater than substantially ½ d.

It will be appreciated that the other embodiments described in conjunction with FIGS. 9A-9E and FIGS. 25D-25E may similarly apply here as well.

Referring further to the drawings, FIGS. 29A-29C illustrate side, proximal, and perspective views, respectively, of an inner conductor 140, in accordance with yet another embodiment of the present invention, wherein the at least one feature 142 is a circular wire construction, issuing from an inner conductor 140 and bent into shapes that define the size d, when viewed from the proximal end 121, formed of the conductive wire of the wire diameter δ, no greater than substantially ½ d.

It will be appreciated that two or more circular wire constructions may similarly be employed, for example, arranged as two or more concentric wire constructions, bent into shapes that define the size d, when viewed from the proximal end 121.

It will be appreciated that the other embodiments described in conjunction with FIGS. 9A-9E and FIGS. 25D-25E may similarly apply here as well.

Referring further to the drawings, FIGS. 30A-30C illustrate side, proximal, and perspective views, respectively, of an inner conductor 140, in accordance with still another embodiment of the present invention. Accordingly, D is substantially equal to 3d, and the at least one feature 142 is a circular wire construction of the conductive wire of the wire diameter δ, wherein the first sharp edge 141 and the sharp edge 142A formed by the circular wire construction create two concentric circular sharp edges, separated substantially by d, when viewed from the proximal end 121 (FIG. 30B).

It will be appreciated that the other embodiments described in conjunction with FIGS. 9A-9E and FIGS. 25D-25E may similarly apply here as well.

Referring further to the drawings, FIGS. 31A-31C illustrate side, proximal, and perspective views, respectively, of an inner conductor 140, in accordance with yet another embodiment of the present invention. The at least one feature 142 is a spiral wire constructions, which is substantially flat, when viewed from the side (FIG. 35A). Preferably, the spiral is formed of the conductive wire of the wire diameter δ. The sharp edges 142A formed by the spiral wire construction create a spiral of sharp edges 142A, separated substantially by d, when viewed from the proximal end 121 (FIG. 31B).

It will be appreciated that the other embodiments described in conjunction with FIGS. 9A-9E and FIGS. 25D-25E may similarly apply here as well.

Referring further to the drawings, FIGS. 32A-32C illustrate side, proximal, and perspective views, respectively, of an inner conductor 140, in accordance with still another embodiment of the present invention. The at least one feature 142 is a conical spiral wire constructions, as viewed from the side (FIG. 32A). Preferably, the spiral is formed of the conductive wire of the wire diameter δ. The sharp edges 142A formed by the spiral wire construction create a spiral of sharp edges 142A, separated substantially by d, when viewed from the proximal end 121 (FIG. 32B).

It will be appreciated that the other embodiments described in conjunction with FIGS. 9A-9E and FIGS. 25D-25E may similarly apply here as well.

Referring further to the drawings, FIGS. 33A and 33B illustrate a probe 120, wherein the feature 142 is helical spiral wire construction, which is inductively coupled.

Referring further to the drawings, FIGS. 33C and 33D illustrate a probe 120, wherein the feature 142 is flat spiral wire construction, which is inductively coupled.

Referring further to the drawings, FIGS. 34A and 34B illustrate a probe 120, wherein the feature 142 is helical spiral wire construction, which is resistively coupled.

Referring further to the drawings, FIG. 35 schematically illustrates an inner construction of a probe 120 for tissue-edge characterization, with first and second inner conductors 140B and 140C, in accordance with embodiments of the present invention.

Accordingly, the second inner conductor 140C serves as a return path for signals generated at the proximal end 121 of the inner conductor 140. It will be appreciated that the features 142 associated with the first and second conductors may be inductively or resistively coupled.

Referring further to the drawings, FIG. 36 schematically illustrates a proximal view of a probe 120 for tissue-edge characterization, in accordance with an embodiment, based on FIG. 35, and showing a feature 142 associated with the two inner conductors 140B and 140C. In the present example, the feature 142 may be arranged as two combs that are interlaced, each in communication with a different one of the inner conductors. The present example is thus of inductive coupling.

Referring further to the drawings, FIGS. 37A and 37B schematically illustrate proximal views of probes 120 for tissue-edge characterization, in accordance with embodiments, based on FIG. 35, and showing other features 142, associated with the two inner conductors 140B and 140C.

As seen in FIG. 37A, the feature 142 may be arranged as two concentric wire circles, each in communication with a different one of the inner conductors. FIG. 37A illustrates inductive coupling between the two inner conductors, 140B smf 140C.

As seen in FIG. 37B, the feature 142 is in physical communication with both the first and the second inner conductors 140B and 140C. FIG. 37B illustrates resistive coupling between the two inner conductors.

Referring further to the drawings, FIGS. 38-39 schematically illustrate another inner construction of a probe 120 for tissue-edge characterization, with two inner conductors, wherein the two inner conductors 140B and 140C and the conductive outer sleeve 171A are operative in the signal path, in accordance with embodiments of the present invention.

As seen in FIG. 39, the feature 142 may be arranged as three concentric wire circles, two of which being in communication with the two inner conductors 140B and 140C, respectively, and a third being in communication with the conductive outer sleeve 171A.

Referring further to the drawings, FIGS. 40 and 41 schematically illustrate another inner construction of a probe 120 for tissue-edge characterization, with a single inner conductor 140, wherein both the inner conductor 140 and the conductive outer sleeve 17 1A are operative in the signal path.

As seen in FIG. 41, the feature 142 may be arranged as two concentric wire circles, one of which being in communication with the inner conductor 140 and the other being in communication with the conductive outer sleeve 171A.

It will be appreciated, with regard to the embodiments illustrated in FIGS. 35-41, that they may be operable also without the conductive outer sleeve 17 1A.

Figure 42:
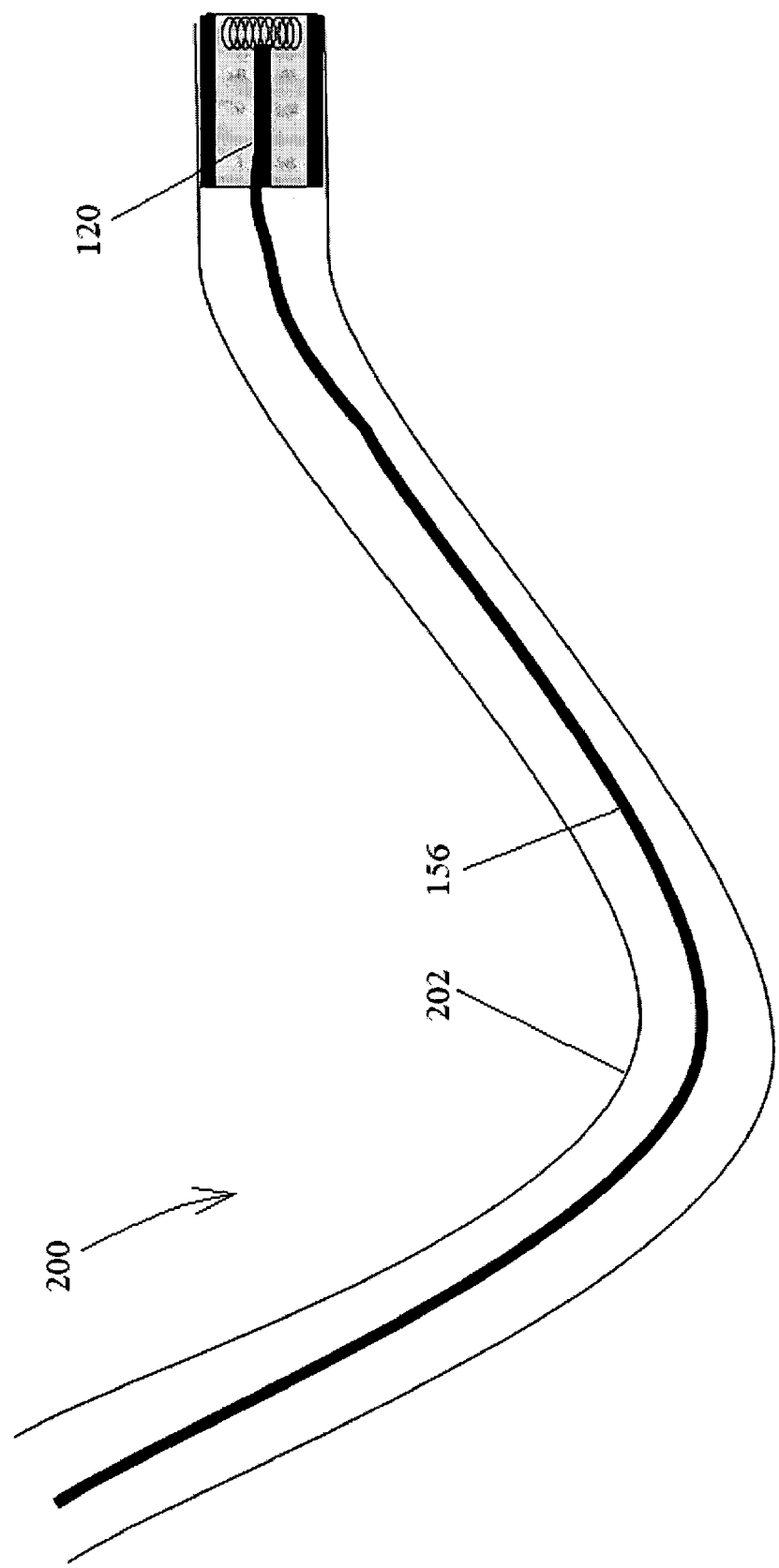
FIG. 42 schematically illustrates a probe fitted within a catheter and operative for intracorporeal insertion, in accordance with an embodiment of the present invention.

In accordance with embodiments of the present invention, the probe 120 may be employed as an extracorporeal probe or as an intracorporeal probe, for example, mounted on an endoscopic tool, as taught in commonly owned U.S. patent application Ser. No. 10/567,581, whose disclosure is incorporated herein by reference. Reference is thus made to FIG. 42, which schematically illustrates a probe fitted within a catheter and operative for intracorporeal insertion, in accordance with an embodiment of the present invention. Accordingly, an intracorporeal system 200 includes the probe 120, associated with the transmission line 156, and fitted within a catheter 202, for intracorporeal insertion, for example, through a body lumen.

It will be appreciated that an intracorporeal probe is also described in commonly owned WO2006/072947, filed on Jan. 4, 2006 and Published on Jul. 13, 2006, incorporated herein by reference.

Figure 43A:
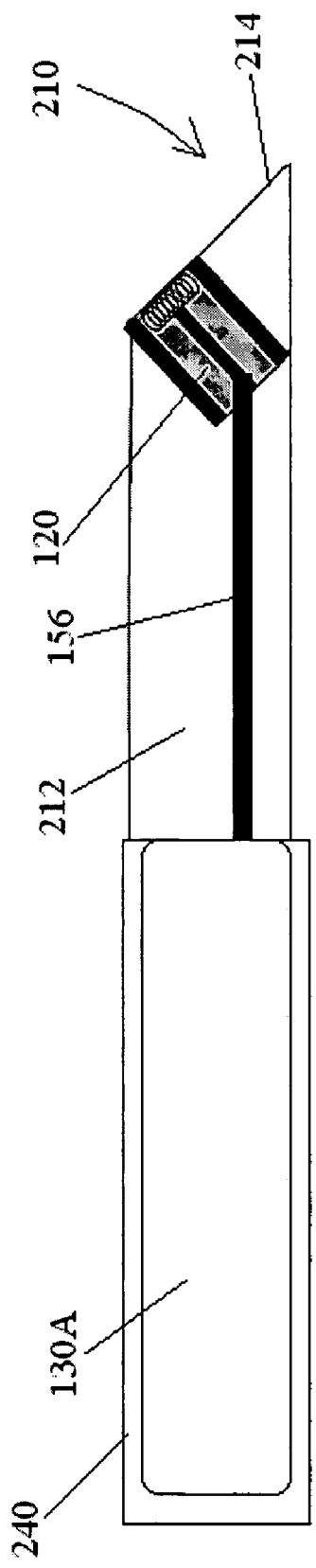
FIGS. 43A and 43B schematically illustrate probes associated with resecting devices, in accordance with embodiments of the present invention.
Figure 43B:
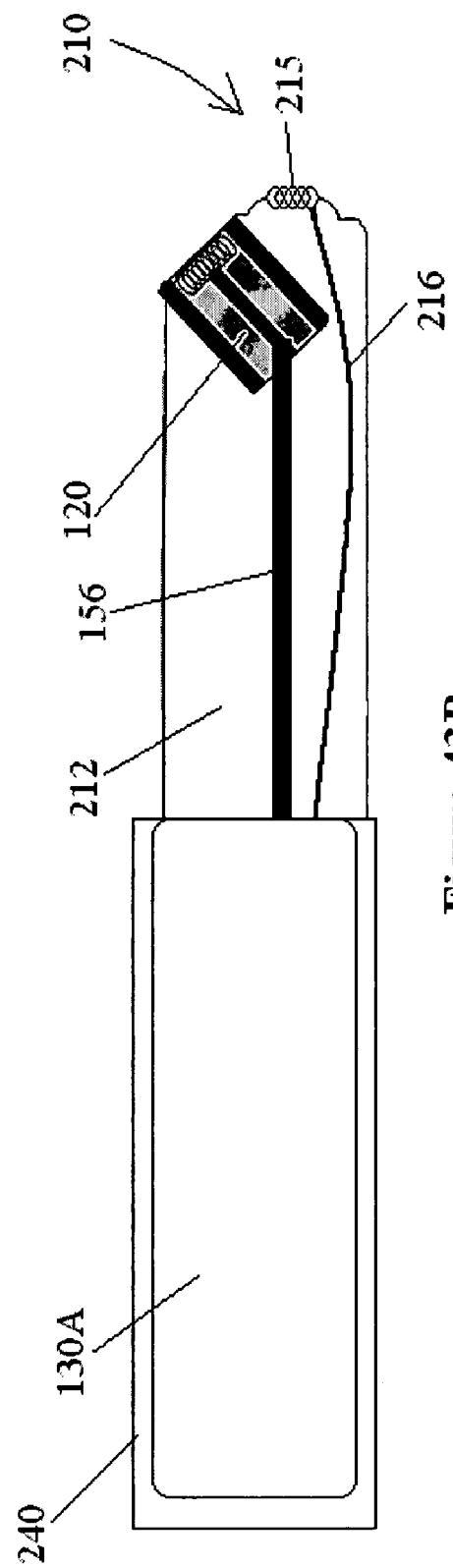

Referring further to the drawings, FIGS. 43A and 43B schematically illustrate probes associated with resecting devices, in accordance with embodiments of the present invention.

FIG. 43A illustrates a probe and resecting tool system 210, which includes the probe 120, associated with the transmission line 156, and mounted on a resecting tool 212, having a cutting edge 214. In this manner, it is possible to characterize a tissue by the probe 120, and where necessary, remove pathological portions of the tissue, by the cutting edge 214. Manipulation of the cutting edge 214 may be manual, via the handle 240. Alternatively, it may be electronic, via the control and instrumentation system 130A, which may be integrated within the handle 240. It will be appreciated that the cutting edge 214 may be controlled via the system 130A, while the probe 120 may be controlled via the control and instrumentation system 130 of FIG. 1.

FIG. 43B illustrates the probe and resecting tool system 210, having a resection device 215, powered by a cable 216. Manipulation of the resection device 215 may be via the control and instrumentation system 130A, integrated within the handle 240, or via the control and instrumentation system 130 of FIG. 1. The resection device 215 may be a coil, designed for hot resection, or it may be a laser device, a cryosurgery device, or any resection device, as known. Again, the probe 120 may be controlled from the control and instrumentation system 130 of FIG. 1, while the resection device 215 may be controlled from the control and instrumentation system 130A within the handle 240.

A probe with a cutting tool is also described in commonly owned U.S. patent application Ser. No. 10/558,831 and in U.S. patent application Ser. 10/891,750, filed on Jul. 15, 2004, now U.S. Pat. No. 7,082,325, issued on Jul. 25, 2006, all of whose disclosures are incorporated herein by reference.

Figure 44A:
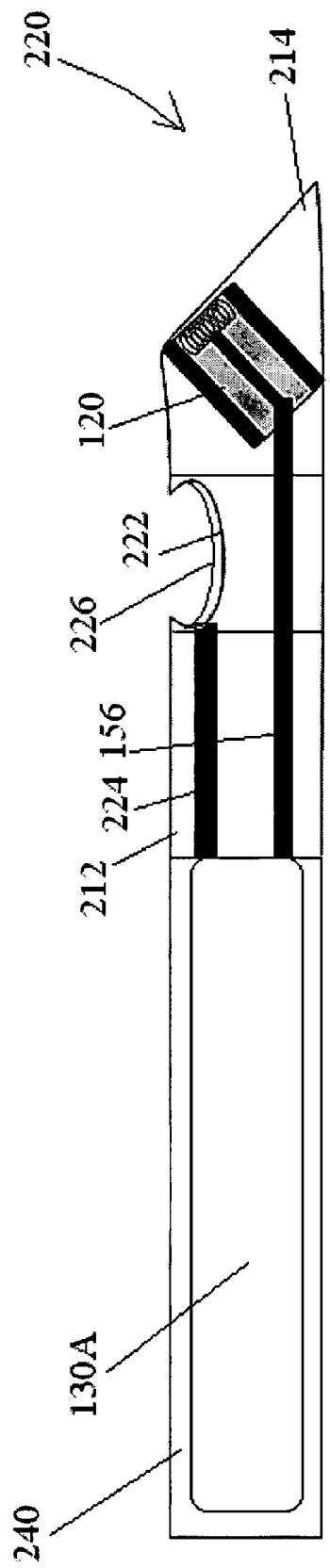
FIGS. 44A and 44B schematically illustrate a probe associated with a biopsy device, in accordance with an embodiment of the present invention.
Figure 44B:
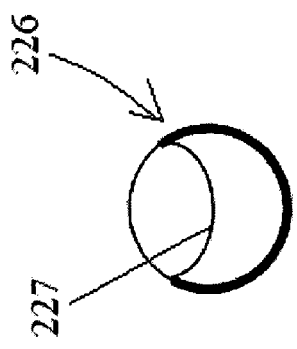

Referring further to the drawings, FIGS. 44A and 44B schematically illustrate a probe associated with a biopsy device, in accordance with an embodiment of the present invention. Accordingly, a probe and biopsy system 220 includes the probe 120, associated with the transmission line 156, and mounted on a biopsy device 220. The biopsy device 220 has a biopsy knife 226, for example, shaped as an ice-cream scoop spoon 226, having a sharp edge 227, and manipulated via a manipulator 224, for collecting tissue samples into a biopsy collection cavity 222. The biopsy system 220 may further include the resecting tool 212. In this manner, it is possible to characterize a tissue by the probe 120, and where necessary, take a biopsy sample, with the biopsy knife 226. If desired, pathological portions of the tissue may be removed by the resecting tool 212. Manipulation of the biopsy device 220 may be manual, or performed from the control and instrumentation system 130A, which may be integrated within the handle 240, or from the control and instrumentation system 130 of FIG. 1. It will be appreciated that the probe 120 may be controlled from the control and instrumentation system 130 of FIG. 1, while the biopsy knife 226 may be controlled from the control and instrumentation system 130A within the handle 240.

It will be appreciated that a biopsy needle may be employed rather than, or in addition to the biopsy knife 226.

It will be appreciated that a probe with a biopsy tool is also described in commonly owned U.S. patent application Ser. No. 10/891,750, filed on Jul. 15, 2004, now U.S. Pat. No. 7,082,325, issued on Jul. 25, 2006, whose disclosure is incorporated herein by reference.

Referring further to the drawings, FIGS. 45A-45D schematically illustrate proximal ends of probes of various shapes, in accordance with embodiments of the present invention.

As seen in FIG. 45A, the proximal end 121 of the probe 120 may be elliptical.

As seen in FIG. 45BA, the proximal end 121 of the probe 120 may be rectangular.

As seen in FIGS. 45C and 45D, the proximal end 121 of the probe 120 may have other shapes, preferably optimized to fit body anatomical constraints. For example, a probe designed for a specific body lumen may be sized and shaped for that particular lumen, for example, the GI tract.

Figure 48:
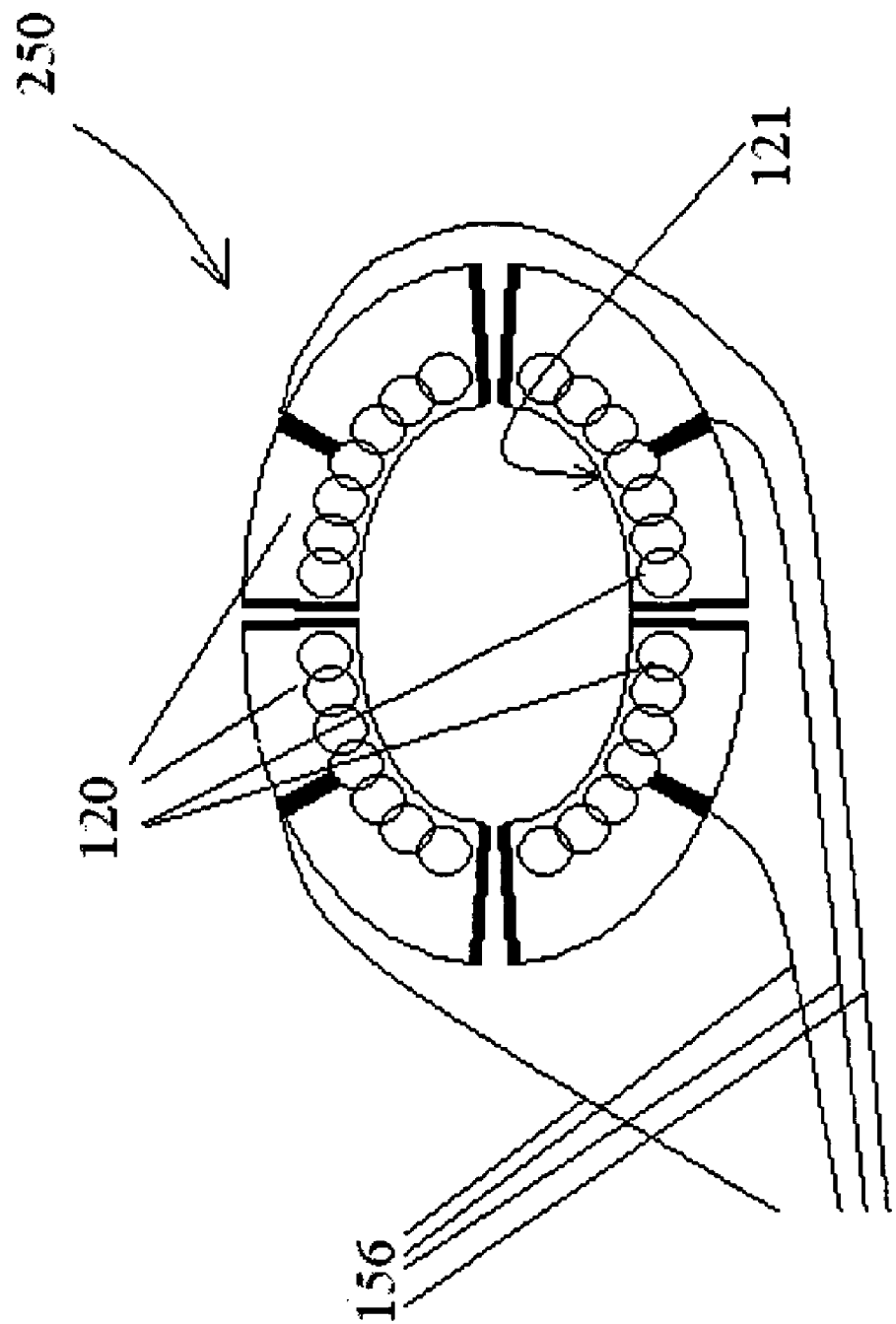
FIG. 48 schematically illustrates an array of probes arranged as a ring, in accordance with an embodiment of the present invention.

Alternatively, the probe may have a specific shape, dedicated to a predetermined tissue specimen shape. For example, if the tissue specimen is extracted by boring, and has a cylindrical shape, the probe may be shaped as a ring or as a tube, with the proximal face 121 on the inner wall of the ring or tube, for optimal contact with the tissue specimen. FIG. 48 hereinbelow illustrates a ring-shaped array 250 of probes 120.

Figure 46A:
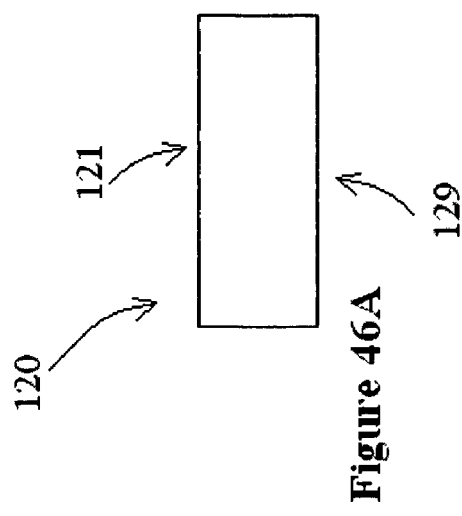
FIGS. 46A and 46B schematically illustrate side views of probes of various shapes, in accordance with embodiments of the present invention.
Figure 46B:
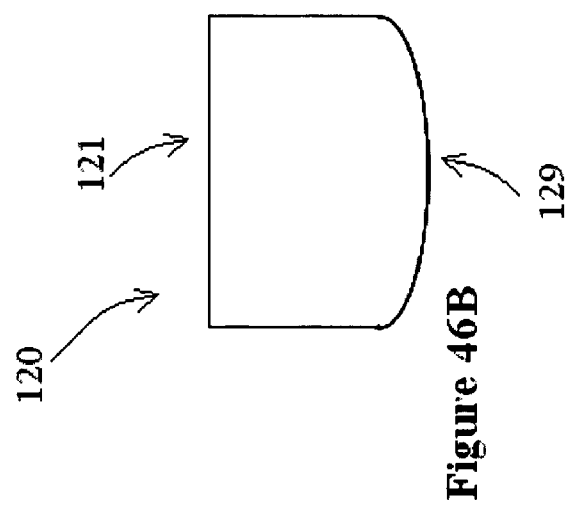

Referring further to the drawings, FIGS. 46A-46B schematically illustrate side views of probes of various shapes, in accordance with embodiments of the present invention.

It will be appreciated that other shapes are similarly possible.

As seen in FIG. 46A, the side view of the probe 120 may be rectangular.

As seen in FIG. 46B the side view of the probe 120 may be concave, at the proximal end 121.

It will be appreciated that shapes other than those described in FIGS. 45A-45D and 46A-46B are possible. Probes of various shapes are also described in commonly owned U.S. patent application Ser. Nos. 11/350,102, 11/196,732, and 10/558,831, all of whose disclosures are incorporated herein by reference.

FIGS. 47A-47F schematically illustrate arrays of probes, each operative as a single testing device for tissue-edge characterization, in accordance with embodiments of the present invention.

FIG. 47A illustrates an array 250 of 3×3 probes 120, while FIG. 47B illustrates an array of 7 probes 120, and FIG. 47C illustrates a row of 3 probes 120, all viewed from their proximal ends 121. It will be appreciated that other arrangements are similarly possible.

Figure 47F:
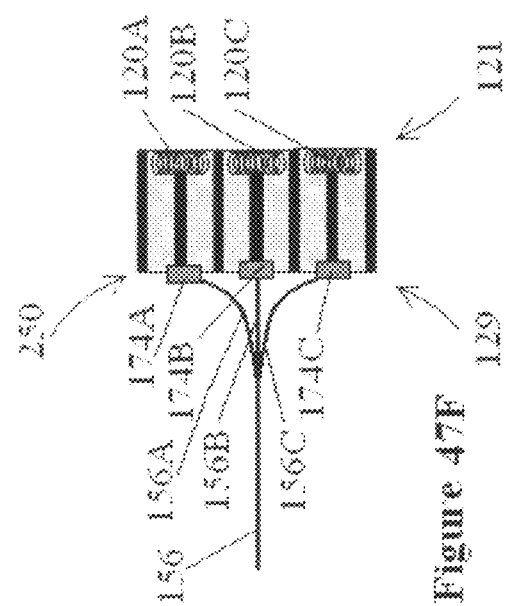
Figure 47D:
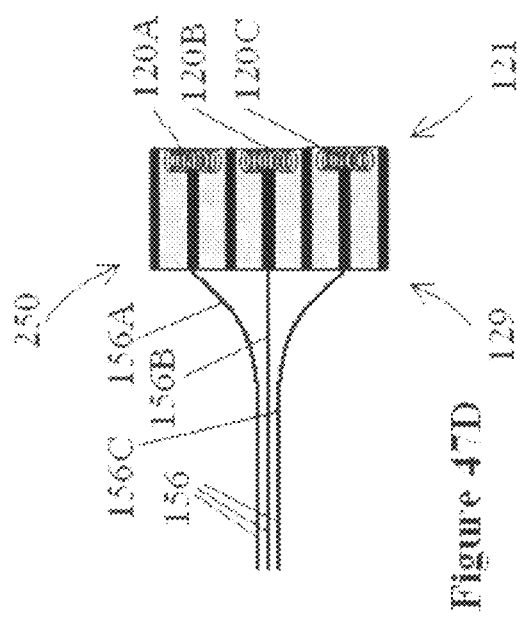
Figure 47E:
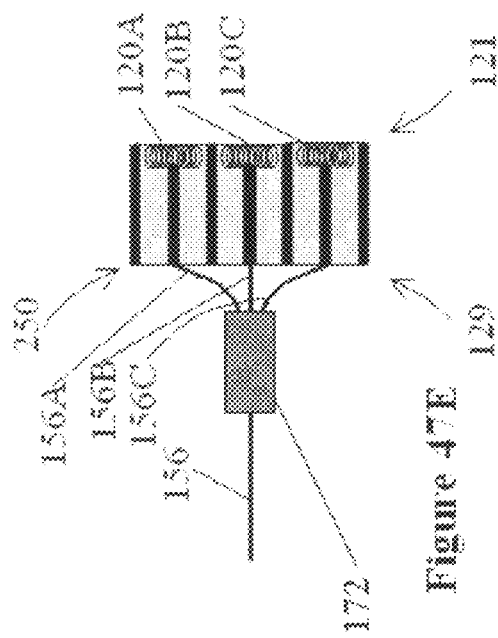

FIGS. 47D-47F illustrate side views of arrays 250 of the probes 120.

As seen in FIG. 47D, each of the probes has a dedicated transmission line. Thus, a probe 120A is associated with a transmission line 156A, a probe 120B is associated with a transmission line 156B, and a probe 120C is associated with a transmission line 156C. Alternatively, as seen in FIGS. 47E and 47F, the single transmission line 156 is employed, with multiplexing, for example, time multiplexing, or wavelength multiplexing. With time multiplexing, a switch 172 is used, operable to selectively route the signals from the transmission line 156 to each of the probes. The switch 172 is located at the point the transmission line 156 branches off, for example, to the transmission line 156A, leading to the probe 120A, the transmission line 156B, leading to the probe 120B, and the transmission line 156C, leading to the probe 120C. With wavelength multiplexing, spectral band-pass filters 174A, 174B, and 174C are placed along the signal paths to each of the probes 120A, 120B, and 120C, respectively, so that only signals within the given band-pass are transferred to, and back, from each of the probes 120. The band-pass filter for each of the probes 120 has a transmission range, with no overlap, so that each of the probes 120 is associated with a different spectral transmission range. By transmitting through the transmission line 156 a signal that covers the full transmission range of all the probes 120, the response of the various probes 120 of the array 250 is obtained.

In a different arrangement still, the probes 120 of the array 250 may be grouped into sub-arrays, and each sub-array may have a dedicated transmission line.

Referring further to the drawings, FIG. 48 schematically illustrates an array of probes arranged as a ring, in accordance with an embodiment of the present invention. It will be appreciated that a single probe 120 may also be shaped as a ring, a tube, or a cone. Additionally, it will be appreciated that the array 250 may take various shapes, for example, for optimal fit of anatomical constraints, or for optimal characterization of tissue of a predetermined tissue specimen shape.

Single testing devices formed as arrays of probes are further described in commonly owned U.S. patent application Ser. Nos. 11/350,102, 11/196,732, and 10/558,831, all of whose disclosures are incorporated herein by reference.

It will be appreciated that the probe 120 may be employed for detecting a clean margin, for example, as taught in commonly owned U.S. patent application Ser. No. 10/558,831, whose disclosure is incorporated herein by reference.

It will be further appreciated that the probe 120 may be employed with effective contact, for example, as taught in commonly owned applications U.S. patent application Ser. Nos. 11/350,102 and 11/196,732, whose disclosures are incorporated herein by reference.

In accordance with embodiments of the present invention, the probe 120 may be employed during surgery.

In accordance with embodiments of the present invention, the feature 142 of the probe 120 may be produced by applying a dielectric layer at the proximal end 121 of the probe, to serve as a substrate, and depositing the feature 142 on the substrate, while providing conductive communication with the conductor 140, or with the first and second conductors 140B and 140C. It will be appreciated that a film of dielectric material may further be applied on the proximal side of the feature 142.

It will be appreciated, with regard to embodiments that do not include the conductive outer sleeve 171A, for example, as illustrated in FIGS. 3A, 3B, and 9A, that in these cases, the fringe field generated in the tissue edge may extend beyond d', which generally defines the depth of the tissue volumetric disk.

Although the present invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

REFERENCES

1. D. J. Winchester and D. P. Winchester. Atlas of Clinical Oncology Breast Cancer. B. C. Decker, Inc. 2000.
2. M. A. Stuchly, et al., "Measurement of Radio Frequency Permitivity of Biological Tissues with an Open-Ended Coaxial Line: Part I and II,"IEEE Trans, Microwave Theory Tech., Vol. MTT-30, pp. 82-92, April 1980.
3. D. Misra, et al., "Non-Invasive Electrical Characterization of Materials at Microwave Frequencies Using Open. Ended Coaxial Line: Test of an improved calibration technique." IEEE Trans. Microwave theory tech. Volume MTT-38, pp. 8-13, January 1990.
4. E. C. Burdette, et al., "In Vivo Probe Measurement Technique for Determining Properties at VHF Trough Microwave Frequencies, " IEEE Trans. Microwave Theory Tech. Vol. MTT-28, pp. 414-427, January 1980.
5. Surowiex, A. J. et al., 1988, Dielectric Properties of Breast Carcinoma and the Surrounding Tissues, IEEE Trans. Biomed. Eng. 35(4):257-262.
6. Heintz, J.& O. Minet, 1995 Dielectric Properties of Female Breast Tumors, In Ninth International Conference on Electrical Bio-Impedance, Heidelberg.
7 Liefn, D. et al., 1998 Clinical Study on Electrical Impedance Method Used Diagnosis of Breast Diasi. In Tenth International Conference on Electrical Bio-Impedance. Barcelona.
8. Morimoto, et al., Measurement of Electrical Bio-Impedance of Breast Tumors, Eu. Serg. Res. 2292:86-92, 1990.
9. S. Grimnes & O. G. Martinsen. "Bioimpedance and Bioelectricity Basic. Academic Press 2000.
10. Kinouch, Y et al., Fast In-Vivo Measurement of Local Tissue Impedance Using Needle Electrodes, Med. Biol Eng. Comput. 35(9):486-492, 1997.
11. Yuken Ohmine, et al., Non-Invasive Measurement of the Electrical Bio-Impedance of Breast Tumors, Anti Cancer Research 20:1941-1946 (2000).
12. Lever-Moskovitz, O. 1996.T-Scan: A New Imaging Method for Breast Cancer Detection Without X-Ray. RSNA., '96, Chicago.
13. Dexter, G. et al, "In-Vivo Measurement of Tumor Conductiveness With Magnetic Bioimpedance Method", IEEE Trans Biomedical Engine", Vol. 47 No. 10 October 2000.
14. Prthig, R., (1978), Dielectric and Electronic Properties of Biological Materials, John Wiley, New York.
15. Schanna, O. F. et al., (1978), Impedance Measurement in Biological Cell. John Wiley, New York.
16. H. P. Schwan, Mechanisms Responsible for Electrical Properties of Tissue and Cell Suspensions, Med. Prog. Tech. 19:163-165, 1993.
17. Fricke, H. The Theory of Electrolytic Polarization. Philosophical Magazine 1932; (97):310-318.
18. Cole K S (1972) Membranes, Ions (1978) and Impulses. University of California Press, Berkeley.

19. Cole, K. S &.Cole. R. H 1941, Dispersion and Absorption in Dielectrics. J. Chem. Phys. 9:341-351.

20. Juan R. Mosig, et al., Reflection of An Open-Ended Coaxial Line and Application to Nondestructive Measurement of Materials. IEEE Trans. Inst. Measr. Vol. IM-30, No. 1, March 1981.

21. U.S. Pat. No. 6,173,604.

22. Xu, Y., et al. "Theoretical and Experimental Study of Measurement of Microwave Permitivity Using Open Ended Elliptical Coaxial Probes". IEEE Trans AP-40(1), January 1992, pp 143-150.3.

23. Proakis, John G., Digital Signal Processing, Chapter 4, Prentice-Hall International Inc.

What is claimed is:

1. A probe for tissue-edge characterization, comprising:
a first inner conductor, which comprises:
proximal and distal ends, with respect to a tissue edge, along an x-axis;
a first sharp edge, located at the proximal end;
at least one feature, issuing from the first inner conductor, at the proximal end, for forming at least one additional sharp edge, operative to enhance localized electrical fringe fields in the tissue, within a predefined tissue volume, at the tissue edge, the tissue volume being defined by physical parameters associated with the at least one feature; and
a dielectric material, which encloses the conductor, in the y-z planes;
wherein the probe is associated with a resecting tool.

2. A probe for tissue-edge characterization, comprising:
a first inner conductor, which comprises:
proximal and distal ends, with respect to a tissue edge, along an x-axis;
a first sharp edge, located at the proximal end;
at least one feature, issuing from the first inner conductor, at the proximal end, for forming at least one additional sharp edge, operative to enhance localized electrical fringe fields in the tissue, within a predefined tissue volume, at the tissue edge, the tissue volume being defined by physical parameters associated with the at least one feature; and
a dielectric material, which encloses the conductor, in the y-z planes;
wherein the probe is shaped for optimal fit of anatomical constraints.

3. A system for tissue-edge characterization, comprising:
a probe for tissue-edge characterization, which comprises:
a first inner conductor, which comprises:
proximal and distal ends, with respect to a tissue edge, along an x-axis;
a first sharp edge, located at the proximal end;
at least one feature, issuing from the first inner conductor, at the proximal end, for forming at least one additional sharp edge, operative to enhance localized electrical fringe fields in the tissue, within a predefined tissue volume, at the tissue edge, the tissue volume being defined by physical parameters associated with the at least one feature; and
a dielectric material, which encloses the conductor, in the y-z planes;
an external control and instrumentation system, for signal generation and signal analysis; and
a transmission line, for connecting between the probe and the external control and instrumentation system, wherein the probe further includes an array of probes, operative as a single testing device for tissue-edge characterization.

4. An array of probes, operative as a single testing device for tissue-edge characterization, wherein each probe of the array is constructed in accordance with claim 3.

5. The array of claim 4, shaped for optimal fit of anatomical constraints.

6. The array of claim 4, wherein each probe is associated with a transmission line.

7. The array of claim 6, wherein each probe is associated with a transmission line, connected to the distal end of the probe's conductor, the transmission line being operative to transmit a signal to the probe's conductor, for applying the electric signals to the tissue, and to transmit back a response signal, which corresponds to primary reflected electric signals.

8. The system of claim 3, wherein the transmission line is a coaxial cable.

9. The system of claim 3, wherein the array is shaped for optimal fit of anatomical constraints.

10. The system of claim 3, wherein the array is shaped for optimal characterization of tissue of a predetermined tissue specimen shape.

11. The system of claim 3, wherein each probe of the array of probes is associated with a transmission line.

12. The system of claim 3, wherein the array of probes is associated with a single transmission line.

13. The system of claim 3, wherein the probe is associated with a resecting tool.

14. The system of claim 3, wherein the probe is shaped for optimal characterization of tissue of predetermined tissue specimen shape.

15. The system of claim 3, wherein the probe is fitted within a catheter for intracorporeal insertion.

16. The system of claim 3, wherein the external control and instrumentation system comprises:
a signal generator, in communication with the probe, via the transmission line, for generating the electric signals;
a detector, in communication with the probe, via the transmission line, for detecting the reflected electric signals; and
a data processor for comparing electrical characteristics of the reflected electric signals with respect to the applied electric signals to produce an indication of the dielectric properties of tissue for examination.

17. The system of claim 16, wherein the electric signals are selected from the group consisting of: a sinusoidal signal, a square pulse, a triangular pulse, a chirped pulse, a modulated pulse, a tailored pulse, and a combination thereof.

18. The system of claim 16, wherein the signal generator is configured for generating and applying electric signals of duration of the order of nanoseconds.

19. The system of claim 16, wherein the signal generator is configured for generating and applying electric signals of duration of the order of picoseconds.

20. The system of claim 16, wherein:
the signal generator is configured for generating and applying a series of the electric signals at a pulse repetition rate of a few Herz to a few giga-Herz.

21. The system of claim 16, wherein:
the detector is configured for detecting the primary reflected electric signals; and
the data processor is configured for comparing the primary reflected electric signals with the applied electric signals, to provide an indication of the impedance of the generally predefined tissue volume, at the tissue edge.

22. The system of claim 16, wherein:
the detector is configured for detecting the primary reflected electric signals; and
the data processor is configured for comparing the primary reflected electric signals with the applied electric signals, to provide an indication of the dielectric properties of the generally predefined tissue volume, at the tissue edge.

23. The system of claim 16, wherein the detector is a digitizing unit.

24. The system of claim 3, configured for sensing in real time.

25. The method of claim 24, wherein the array is shaped for optimal characterization of tissue of a predetermined tissue specimen shape.

26. A system for tissue-edge characterization, comprising:
a probe for tissue-edge characterization, which comprises:
  a first inner conductor, which comprises:
    proximal and distal ends, with respect to a tissue edge, along an x-axis:
    a first sharp edge, located at the proximal end;
    at least one feature, issuing from the first inner conductor, at the proximal end, for forming at least one additional sharp edge, operative to enhance localized electrical fringe fields in the tissue, within a predefined tissue volume, at the tissue edge, the tissue volume being defined by physical parameters associated with the at least one feature; and
  a dielectric material, which encloses the conductor, in the y-z planes;
an external control and instrumentation system, for signal generation and signal analysis; and
a transmission line, for connecting between the probe and the external control and instrumentation system, wherein the probe is associated with a biopsy device.

27. A system for tissue-edge characterization, comprising:
a probe for tissue-edge characterization, which comprises:
  a first inner conductor, which comprises:
    proximal and distal ends, with respect to a tissue edge, along an x-axis:
    a first sharp edge, located at the proximal end;
    at least one feature, issuing from the first inner conductor, at the proximal end, for forming at least one additional sharp edge, operative to enhance localized electrical fringe fields in the tissue, within a predefined tissue volume, at the tissue edge, the tissue volume being defined by physical parameters associated with the at least one feature; and
  a dielectric material, which encloses the conductor, in the y-z planes;
an external control and instrumentation system, for signal generation and signal analysis; and
a transmission line, for connecting between the probe and the external control and instrumentation system, wherein the probe is shaped for optimal fit of anatomical constraints.

28. A method for tissue-edge characterization, comprising:
providing a probe for tissue-edge characterization, comprising:
  a first inner conductor, which comprises:
    proximal and distal ends, with respect to a tissue edge, along an x-axis;
    a first sharp edge, located at the proximal end;
    at least one feature, issuing from the first inner conductor, at the proximal end, for forming at least one additional sharp edge, operative to enhance localized electrical fringe fields in the tissue, within a predefined tissue volume, at the tissue edge, the tissue volume being defined by physical parameters associated with the at least one feature; and
  a dielectric material, which encloses the conductor, in the y-z planes;
bringing the probe to form contact with the tissue edge;
applying electric signals, associated with a wavelength $\lambda$, to the tissue;
generating the enhanced localized electrical fringe fields in the tissue, within the generally predefined tissue volume, at the tissue edge;
producing primary reflected electric signals from the tissue, substantially only from the predefined tissue volume, at the tissue edge; and
sensing the primary reflected electric signals, from the predefined tissue volume, at the tissue edge, wherein the probe further includes an array of probes, operative as a single testing device for tissue-edge characterization.

29. The method of claim 28, wherein the array is shaped for optimal fit of anatomical constraints.

30. The method of claim 28, wherein the probe is associated with a resecting tool.

31. The method of claim 28, wherein the probe is shaped for optimal characterization of tissue of predetermined tissue specimen shape.

32. The method of claim 28, wherein the probe is fitted within a catheter for intracorporeal insertion.

33. A method for tissue-edge characterization, comprising:
providing a probe for tissue-edge characterization, comprising:
  a first inner conductor, which comprises:
    proximal and distal ends, with respect to a tissue edge, along an x-axis:
    a first sharp edge, located at the proximal end;
    at least one feature, issuing from the first inner conductor, at the proximal end, for forming at least one additional sharp edge, operative to enhance localized electrical fringe fields in the tissue, within a predefined tissue volume, at the tissue edge, the tissue volume being defined by physical parameters associated with the at least one feature; and
  a dielectric material, which encloses the conductor, in the y-z planes;
bringing the probe to form contact with the tissue edge;
applying electric signals, associated with a wavelength $\lambda$, to the tissue;
generating the enhanced localized electrical fringe fields in the tissue, within the generally predefined tissue volume, at the tissue edge;
producing primary reflected electric signals from the tissue, substantially only from the predefined tissue volume, at the tissue edge; and
sensing the primary reflected electric signals, from the predefined tissue volume, at the tissue edge, wherein the probe is associated with a biopsy device.

34. A method for tissue-edge characterization, comprising:
providing a probe for tissue-edge characterization, comprising:
  a first inner conductor, which comprises:
    proximal and distal ends, with respect to a tissue edge, along an x-axis:
    a first sharp edge, located at the proximal end;
    at least one feature, issuing from the first inner conductor, at the proximal end, for forming at least one additional sharp edge, operative to enhance localized electrical fringe fields in the tissue, within a predefined tissue volume, at the tissue edge, the tissue volume being defined by physical parameters associated with the at least one feature; and a dielectric material, which encloses the conductor, in the y-z planes;
bringing the probe to form contact with the tissue edge;
applying electric signals, associated with a wavelength $\lambda$, to the tissue;
generating the enhanced localized electrical fringe fields in the tissue, within the generally predefined tissue volume, at the tissue edge;
producing primary reflected electric signals from the tissue, substantially only from the predefined tissue volume, at the tissue edge; and
sensing the primary reflected electric signals, from the predefined tissue volume, at the tissue edge, wherein the probe is shaped for optimal fit of anatomical constraints.

* * * * *